(12) United States Patent
Quentin

(10) Patent No.: US 7,405,280 B2
(45) Date of Patent: Jul. 29, 2008

(54) CHROMOGENIC SUBSTANCES AND USE THEREOF FOR THE DETERMINATION OF CARBOXYPEPTIDASE ACTIVITIES

(75) Inventor: Gérard Quentin, Yevres (FR)

(73) Assignee: Diagnostica Stago (FR)

( * ) Notice: Subject to any disclaimer, the term of this patent is extended or adjusted under 35 U.S.C. 154(b) by 259 days.

(21) Appl. No.: 10/751,601

(22) Filed: Jan. 5, 2004

(65) Prior Publication Data

US 2005/0107305 A1 May 19, 2005

Related U.S. Application Data

(63) Continuation of application No. PCT/FR02/02376, filed on Jul. 5, 2002.

(30) Foreign Application Priority Data

Jul. 6, 2001 (FR) .................................. 01 09030

(51) Int. Cl.
*C07K 5/06* (2006.01)
*C07K 5/065* (2006.01)
*C12Q 1/37* (2006.01)

(52) U.S. Cl. .................. 534/738; 534/770; 534/787; 534/794; 534/798; 534/885; 435/24

(58) Field of Classification Search ............... 534/738, 534/770, 787, 794, 798, 885; 435/24
See application file for complete search history.

(56) References Cited

U.S. PATENT DOCUMENTS 4,551,272 A * 11/1985 Sugiyama et al. ........... 562/445
6,461,832 B2 * 10/2002 Gilvarg ....................... 435/24

OTHER PUBLICATIONS

Mock and Xu, "Catalytic activity of carboxypeptidase B and of Carboxypeptidase Y with anisylazoformyl substrates," Bioorganic & Medicinal Chemistry Letters, vol. 9, pp. 187-192. (1999)/.
Mock et al., "Arazoformyl peptide surrogates as spectrophotometric kinetic assay substrates for carboxypeptidase A," Analytical Biochemistry, vol. 239, pp. 218-222 (1996).
Mock and Stanford, "Arazoformyl dipeptide substrates for thermolysin. Confirmation of a reverse protonation catalytic mechanism," Biochemistry vol. 35 No. 23 pp. 7369-7377 (1996).

Schatteman et al., "Assay of procarboxypeptidase U, a novel determinant of the fibrinolytic cascade, in human plasma," Clinical Chemistry vol. 45, No. 6 pp. 807-813 (1999).

* cited by examiner

*Primary Examiner*—Fiona T Powers
(74) *Attorney, Agent, or Firm*—Lerner, David, Littenberg, Krumholz & Mentlik, LLP

(57) ABSTRACT

The invention relates to chromogenic compounds and the use thereof for the determination of enzymes of the family of carboxypeptidases N and carboxypeptidases U. The above is more specifically a compound of formula (I) in which $A=(1)$, (2), (3), (4) or (5), $R1, R2=H$, $-CH_3$, $-CH(CH_3)_2$, $-OCH_3$, $-Cl$, $-CF_3$, $-OCF_3$, $-SCH_3$, $R_3=$an amino acid group which may be hydrolysed by a carboxypeptidase A and $R_4=$a basic amino acid group.

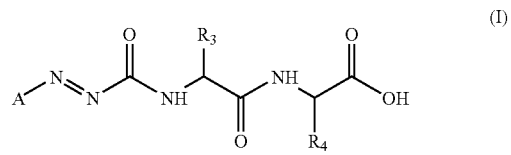

(I)

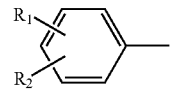

(1)

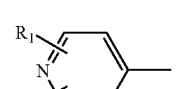

(2)

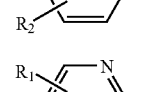

(3)

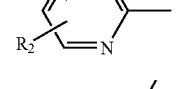

(4)

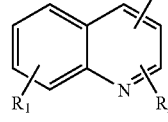

(5)

39 Claims, 8 Drawing Sheets

KEY: Spectre du = Spectrum of

KEY: Spectre du = Spectrum of

KEY: Spectre du = Spectrum of

R = Arginine
F = Phenylalanine

KEY: *Delta DO = Delta OD; Concentration en µg/ml = Concentration in µg/ml*

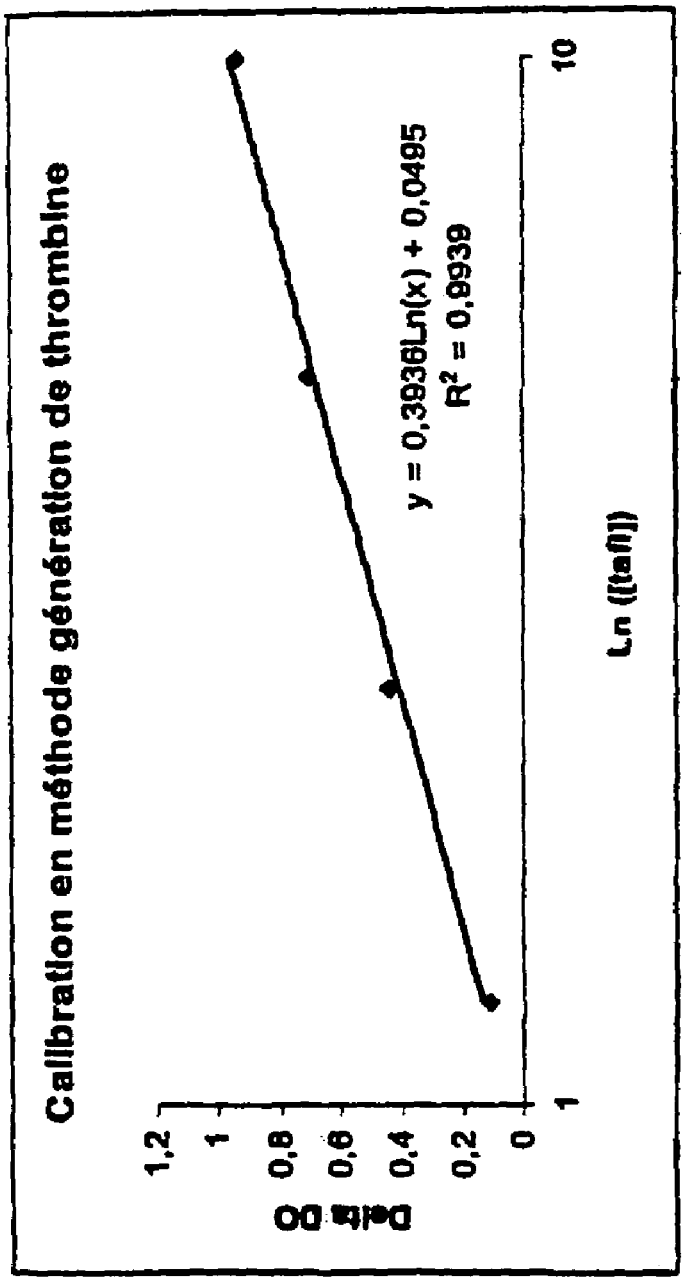
Figure 4 : Calibration in the method of thrombin generation Colorimetric dosage with chromogenic substrate : 4-MTPAFYR
KEY: *Delta DO = Delta OD*

CHROMOGENIC SUBSTANCES AND USE THEREOF FOR THE DETERMINATION OF CARBOXYPEPTIDASE ACTIVITIES

The present invention relates to chromogenic compounds and their use in assaying enzymes from the carboxypeptidase N and carboxypeptidase U family. More specifically, it relates to the use of said compounds in assaying the activity of TAFI (Thrombin Activatable Fibrinolysis inhibitor) in a blood sample, and to the corresponding assay method.

Carboxypeptidases (CP) constitute a group of enzymes in the exopeptidase family. They are enzymes which cleave the amide bonds in polypeptide chains at the last COOH-terminal amino acid. They comprise the serine carboxypeptidases, the cysteine carboxypeptidases and the metallocarboxypeptidases.

Many carboxypeptidases have been isolated and sequenced, in bacteria, yeasts and plants. Those enzymes are also present in a wide variety of tissues in mammals.

Carboxypeptidases have been isolated from the pancreas and from most cells. Other carboxypeptidases circulating in the plasma have also been cloned, isolated and sequenced.

All of those enzymes play an in vivo role depending both on their location and their physical properties. Carboxypeptidases are thus classified differently according to their substrate specificity. Carboxypeptidases A have a relatively broad spectrum: they preferentially hydrolyze the C-terminal peptide bond of the last amino acid if it is hydrophobic (Phe, Leu, Val, Ala). They hydrolyze dicarboxylic amino acids (Asp, Glu) more slowly, also glycine (Gly), and do not hydrolyze at all basic amino acids such as arginine (Arg), lysine (Lys), histidine (His) or ornithine (Orn), a lower homologue of lysine, nor secondary amino acids such as proline (Pro) or hydroxyproline (Hyp).

Carboxypeptidases B specifically hydrolyze the last basic C-terminal amino acids such as Arg, Lys. This class of enzymes is subdivided into sub-classes constituted by carboxypeptidases H (also known as enlephalin convertase or carboxypeptidase E), M, N and U.

Carboxypeptidase E has been located in the secretory granules of the pancreatic islets, the surrenal glands and the pituitary glands, and in the brain. Carboxypeptidase M is a membrane enzyme present in many cultured tissues and cells.

Carboxypeptidase N (hereinafter termed CPN) is an enzyme circulating in the plasma. It protects the organism against the vasoactive and inflammatory effect of peptides containing a basic C-terminal amino acid (preferably a lysine) liberated in the circulation. This enzyme exists in its active form in the blood. It is also termed kininase because of its natural substrates, namely bradykinin, kinine and anaphylatoxins.

Finally, U (unstable) carboxypeptidases (hereinafter termed CPU) are enzymes which also hydrolyze basic C-terminal amino acids with a preference for arginines but which, in contrast to carboxypeptidase N, are highly unstable when they are in their activated form.

A recent general review concerning enzymes from the carboxypeptidase family has been carried out by BOUMA et al (1).

TAFI is a basic zinc metallocarboxypeptidase (1-4). More precisely, it is a carboxypeptidase U, as its activity is unstable at 37° C. This enzyme, including its cDNA and the corresponding amino acid sequence in man, have been described, for example, in U.S. Pat. No. 5,206,161, is a plasma protein the role of which in regulating fibrinolysis was initially envisaged by in vitro observation of a delay in lysis of a clot in the presence of activated TAFI.

Activated TAFI cleaves arginine and lysine residues exposed in the COOH-terminal position of fibrin. This hydrolysis results in a reduction in the number of plasminogen and tPA binding sites on the surface of the fibrin clot, and thus a reduction in the transformation of plasminogen to plasmin by the tPA.

TAFI was successively identified as procarboxypeptidase B (pro-PCPB) then as unstable procarboxypeptidase (proCPU: Unstable ProCarboxypeptidase) and procarboxypeptidase R (CPR), because of carboxypeptidase activity on arginine residues. The zymogenic form is a glycoprotein with a single 60 kDa chain synthesized in the liver and circulating in the plasma.

The zymogen is primarily cleaved by thrombin at the arg 92 site. This proteolysis liberates a 92 amino acid N-terminal peptide containing several glycosylation sites. The catalytic action of thrombin on TAFI is considerably increased by thrombomodulin in the presence of divalent ions. The rate of activation of TAFI catalyzed by thrombin is thus increased more than 1000 fold because of the formation of a ternary complex with thrombomodulin.

Activated TAFI (TAFIa) is constituted by a C-terminal catalytic region of the zymogen and comprises 309 amino acids.

Because of its key role in mechanisms regulating the fibrinolysis process, it is rapidly confirmed that it was useful to be able to measure the quantity of constitutional activated TAFI and activatable TAFI present in the plasma in different pathological conditions.

Several methods for assaying the activity of various carboxypeptidases using specific substrates have been described in the prior art.

WOLFF et al. (5) compared the performances of the synthetic substrates Hip-Arg, Hip-Lys, Hip-Orm on pancreatic B carboxypeptidases purified by chromatography by measuring differences in UV absorption.

In 1970, S. SUZUKI et al. (6) improved the detection of the hydrolysis product by derivatisating of the benzoylglycine liberated by the reagent TT (2,4,6-Trichloro-5-Triazine). This derivation operated specifically on the $CH_2$ of the glycine in a to only a single free acid function. This derivative went bright yellow (maximum wavelength at 382 nm).

This method for developing a yellow coloration on the Hippuryl residues was widely used by several subsequent authors.

In 1972, K. LORENTZ et al. (7) used an arginine coloration reaction, this time liberated by the action of B carboxypeptidases on a Hip-Arg substrate using p-benzoquinone as a reagent. In this way, the colored derivative had a maximum wavelength at 480 nm.

In 1980, Th. H. Plummer et al. (8) used a synthetic substrate: furylacryloyl-Ala-Lys, to quantify carboxypeptidases N, read at 324 nm (close UV but not visible).

In 1985, G. H. Fischer et al. (9) used a fluorescent substrate by N-terminal dansylation of a specific peptide of the carboxypeptidase to be assayed. This assay necessitates a step for extracting hydrolysis products for good separation of the species prior to reading.

In 1986, H. SARUTA et al.determined, by a calorimetric method, the activity of carboxypeptidase A (10). They used a specific enzyme: "Hippuricase" to hydrolyse the hippuricyl derivative itself obtained by hydrolysis of the hydroxyl-hippuricyl-Phg substrate using CPA. This reaction was finally revealed by 4-aminoantipyrine to give a quinoneimide colorant absorbing at 505 nm.

In 1998, NAM JOO HONG et al. used a synthetic substrate with an arginine analogue, thiaarginine, to assay CPBs (11).

However, the colorimetric methods described above either have never been used to specifically assay the enzymatic activity of CPN or CPU, in particular TAFI, or have certain disadvantages that are incompatible with a simple effective assay test of that type of enzyme by colorimetry.

In fact, depending on the case:
- either the derivatisation reaction resulting in a colored product is not specific to the species released during hydrolysis;
- or the derivatisation reagents are highly toxic and cannot be used on an industrial scale;
- or the colored development method is too lengthy and restrictive and cannot readily be automated.

In 1996, W. L. Mock et a,. described a method for assaying an extracellular zinc endoprotease of bacterial origin, thermolysin, using synthetic substrates that decolorized under the action of enzymatic hydrolysis (12). To this end, the authors synthesized dipeptide compounds constituted by a leucine residue carrying a N-(4-methoxyphenylazoformyl) group grafted at the amine function, and a further neutral amino acid (Leu, Ala, Phe or Gly).

Incorporating the arazoformyl group gave rise to a highly colored compound. In the presence of thermolysin, the colorant molecule rearranges during the chemical hydrolysis reaction in accordance with a mechanism that has been well described in (12-13), giving rise to non-colored products (anisole fragment, $N_2$, $CO_2$ and amino acid). It is thus easy to follow the enzyme velocity using the rate of medium decolorization.

The same authors also described a kinetic method for assaying by spectrophotometry based on the same principle as before for carboxypeptidase A (13) and porcine pancreatic carboxypeptidase B (14).

In that case, the compounds used were constituted by a single amino acid known to be cleaved by carboxypeptidase A (Phe, Leu) or carboxypeptidase B (Lys), carrying a N-arazoformyl group. Enzymatic cleavage of those compounds to non colored products was followed by measuring the decrease in coloration of the medium.

Starting from this information, the authors of the present invention have synthesized novel colored compounds for assaying the activity of the carboxypeptidase N or carboxypeptidase U, more particularly the activity of TAFI, by a colorimetric method.

In a first aspect, then, the present invention concerns novel compounds constituting substrates for carboxypeptidase N or U, more particularly substrates of activated TAFI. These compounds are chromogenic substrates.

The compounds of the invention are characterized in that they are arazoformyl compounds with the following general formula (I):

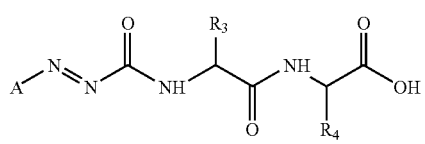

in which:

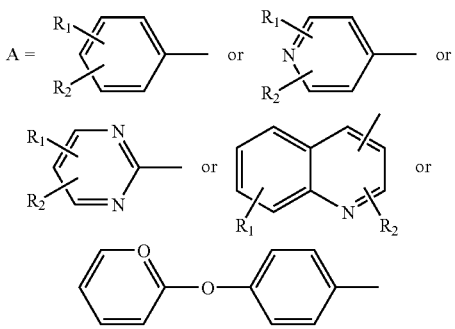

$R_1$, $R_2$=H, —$CH_3$, —$CH(CH_3)_2$, —$OCH_3$, —Cl, —$CF_3$, —$OCF_3$, —$SCH_3$;
$R_3$=an amino acid radical hydrolysable by a carboxypeptidase A;
$R_4$=a basic amino acid radical.

More particularly, $R_3$ is selected from hydrophobic amino acid radicals such as:

tyrosine:

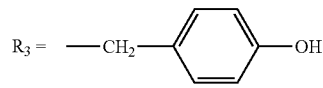

phenylalanine:

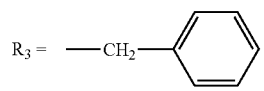

alanine: $R_3$=—$CH_3$;
valine: $R_3$=—CH—$(CH_3)_2$;
leucine: $R_3$=—$CH_2$—CH—$(CH_3)_2$;
isoleucine: $R_3$=—CH—$CH_2$—$CH_3$;
         $CH_3$
phenylglycine:

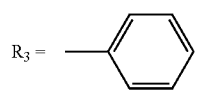

More precisely, $R_4$ is selected from amino acid radicals such as:
arginine:

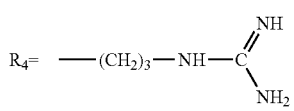

lysine: $R_4$=—$(CH_2)_4$—$NH_2$;
ornithin: $R_4$=$(CH_2)_3$—$NH_2$

Preferably, $R_3$ represents an aromatic amino acid residue and in particular phenylalanine or tyrosine, and $R_4$ represents arginine or lysine.

Preferably, $R_1$ is selected from:
—H and —$CH_3$; and
$R_2$ is preferably selected from:
—$CH_3$, —O—$CH_3$ and —S—$CH_3$.

A preferred family of compounds of the invention is represented by the general formula:

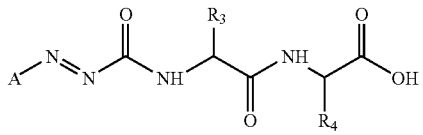

in which:
A=

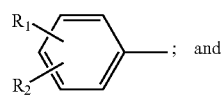
; and and
$R_1$, $R_2$=—H, —$CH_3$, $(CH_3)_2CH$—, $CH_3$—O—, Cl—, —$CF_3$;
$R_3$=an amino acid radical hydrolysable by a carboxypeptidase A;
$R_4$=a basic amino acid radical.

Preferably, $R_3$ represents phenylalanine or tyrosine; and $R_4$ preferably represents arginine or lysine.
Preferably, $R_1$ is selected from:
—H and —$CH_3$; and
$R_2$ is preferably selected from:
—$CH_3$, —O—$CH_3$ and —S—$CH_3$.

A particularly preferred compound from the family defined in the present invention is a compound with formula (I) in which:
A=

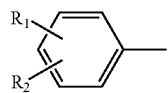

said compound being selected from the group constituted by the following compounds, in which:

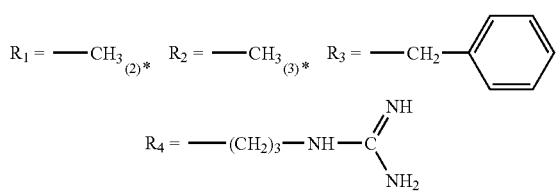

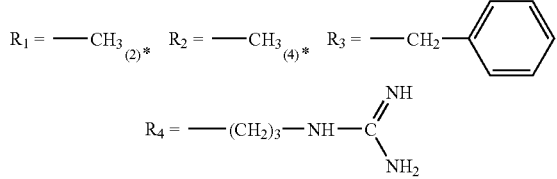

-continued

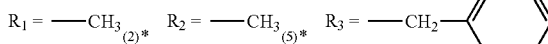
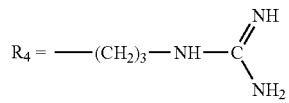

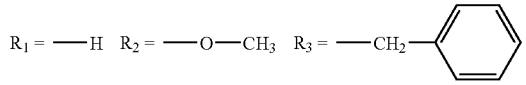
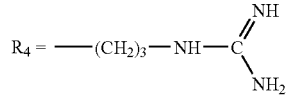

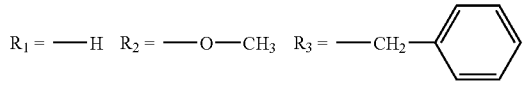
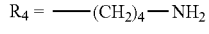

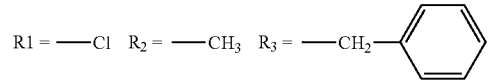
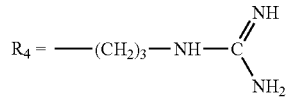

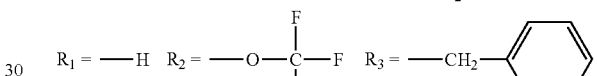
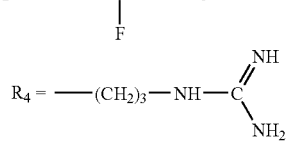

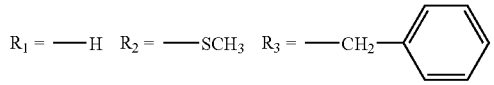
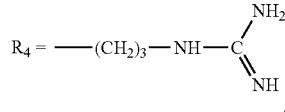

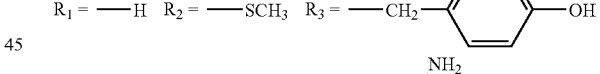
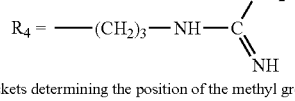

* the numbers in brackets determining the position of the methyl groups on the phenyl radical.

In particular, within the context of the definitions given above, the invention concerns every compound with formula (I) resulting from the possible combinations of groups A, $R_1$, $R_2$, $R_3$ and $R_4$ a preferred definition of which was given above.

In the following description, the compounds as defined will equally be termed "compounds with formula (I)" or "substrates with formula (I)".

In a second aspect, the present invention concerns a method for colorimetric assay of the activity of a carboxypeptidase N, or preferably the activity of a CPU, in a biological sample in which:
said sample is brought into contact with a chromogenic compound with formula (I) as defined above, and an enzyme from the carboxypeptidase A family, under conditions that allow hydrolysis of the sample; and hydrolysis of said compound with formula (I) by the CPN or CPU of the sample is determined by measuring the decrease in its coloration (corresponding to a reduction in absorption) at a wavelength selected from the absorption spectrum of said compound.

On the one hand, the reduction in coloration results from double hydrolysis of the substrate with formula (I) by the carboxypeptidase N or U of the sample and, on the other, by carboxypeptidase A.

The method of the present invention is preferably carried out using a compound with formula (I) in which the hydrophobic amino acid is phenylalanine or preferably, tyrosine, and the basic amino acid is arginine or lysine.

The method of the invention is preferably implemented using a compound with formula (I) in which $R_1$ is selected from —H and —$CH_3$ and $R_2$ is selected from —$CH_3$, —O—$CH_3$ and —S—$CH_3$. Advantageously, when $R_1$ is H in the compound with formula (I), $R_2$ is S—$CH_3$.

The method of the present invention is advantageously implemented with the family of compounds with formula (I) in which:

-A=

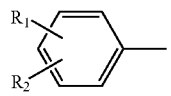

$R_1$ and $R_2$ having any of the meanings given above and $R_2$ preferably being —S—$CH_3$.

More particularly, the compound with formula (I) is a phenylazoformyl compound in which:

-A=

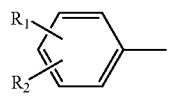

said compound being selected from the group constituted by the following compounds, in which:

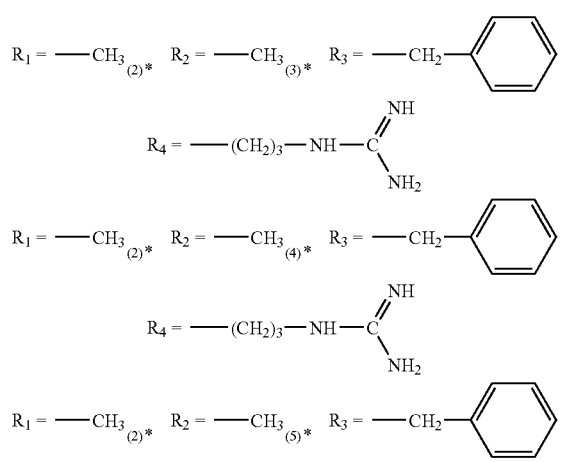

-continued

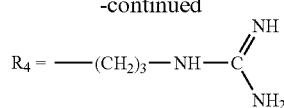
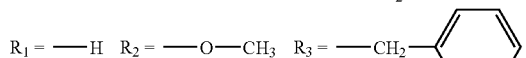
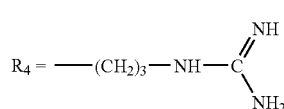
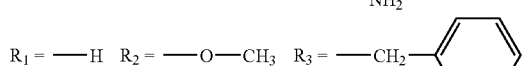
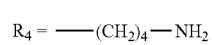
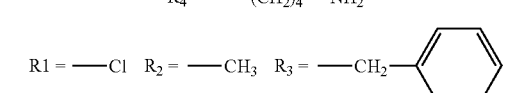
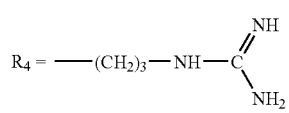
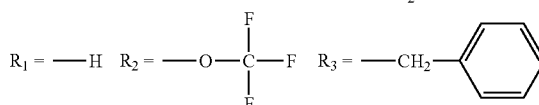
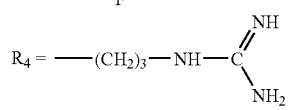
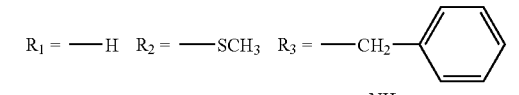
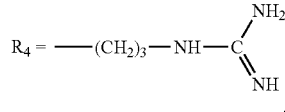
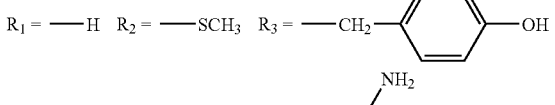
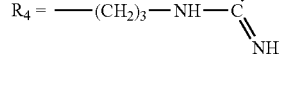

the numbers in brackets determining the position of the methyl groups on the phenyl radical.

The carboxypeptidase A used can derive from different sources, such as for example the pancreas or mast cells. It may be of human or animal origin.

Preferably, pancreatic carboxypeptidase A of bovine origin is used in the context of the invention.

The principle of the method of the invention is based on hydrolysis of a colored substrate with formula (I) as described above, by the action of carboxypeptidase N or carboxypeptidase U that may be present in the analyzed sample, associated with that of carboxypeptidase A added to the medium. This specific hydrolysis leads to an extinction of the coloration of the starting compound, which may be followed using a spectrophotometer.

More precisely, depending on the hydrolysis specificities of carboxypeptidases N or U and A described above, and the structural characteristics of the compounds with formula (I) described above, contact of a carboxypeptidase A and an activated carboxypeptidase N or U with said compound will generate cleavage at the bond between the first and second amino acid of said compound due to the action of the carboxypeptidase N or U, followed almost simultaneously by cleavage at the bond between the azoformyl group and the first amino acid, because of the action of carboxypeptidase A.

The resultant of the two reactions will be decolorization of the starting medium. It will thus be easy to follow, as a function of time, this decrease in color by observing at an absorption wavelength of the colorant [compound with formula (I)], preferably at the wavelength corresponding to its maximum (peak) absorption.

This decrease is representative of the hydrolysis kinetic. The quantity of active carboxypeptidase N or U initially present in the sample is calculated by comparing the measured optical density with that of a calibration curve which can, for example, be established from a range of concentrations of purified active carboxypeptidase N or U in solution.

In contrast, if the sample does not contain carboxypeptidase N or U or if it is inactive, there will be no cleavage between the first and second amino acid of the compound with formula (I) and thus carboxypeptidase A cannot act at the bond of the colored group on the first amino acid. Thus, no decrease in the coloration of the starting solution will be observed.

More particularly, the invention provides a method for assaying the activity of a CPN or CPU in a biological sample, in particular a blood sample such as whole blood or pure or diluted plasma, and preferably a method for assaying the activity of TAFI in a blood sample, in particular pure or diluted plasma.

In this case, the test sample is initially brought into the presence of a buffer solution with, if necessary, a carboxypeptidase activator the activity of which is to be measured (solution hereinafter termed the activator buffer), and left to incubate, for the time necessary to obtain activation of the carboxypeptidase being studied. Preferably, incubation is carried out at ambient temperature for 5 to 20 minutes, advantageously 8 to 12 minutes, preferably 10 minutes.

In a preferred implementation of the invention, the carboxypeptidase activator can be an activator, in particular a coagulation factor, which is allowed to act so as to activate the carboxypeptidase U, in particular TAFI.

In this case, a protease serine inhibitor is then added to the mixture to cause a blockage in the coagulation process. The protease serine inhibitor is, for example, PPACK (H-D-Phe-Pro-Arg-chloromethylketone-Bachem—Ref. No. 1065) used in a final concentration range of 1 to 50 μM, preferably 30 μM, corresponding to initial concentrations of 10 to 250 μM and preferably 150 μM. Other compounds such as Péfabloc [4-(2-aminoethyl)-benzenesulphonylfluoridehypochloride—Penthapharm—Ref. 399.01], preferentially used in a concentration of 0.1 mM, are also suitable.

Simultaneously or immediately after adding the inhibitor, one of the compounds with formula (I) of the invention is added in aqueous solution. This compound is generally used in a final concentrations range of 0.25 to 10 mM, preferably in the range 0.25 to 2.5 mM, advantageously in the range 0.25 to 1 mM. It is preferably used in a concentration of 0.4 mM.

After a new incubation phase, preferably at ambient temperature, during which the substrate with formula (I) will have been cleaved at its second amino acid by the CPN or CPU of the sample the activity of which is to be researched, hydrolysis can be stopped by adding HCl, immediately followed by adding a base to re-adjust the pH to a value in the range 7 to 8.

The optical density of the mixture obtained is then measured a first time without adding CPA to the medium. CPA is then added to the medium, and the OD is measured again. Its decrease can be followed using a spectrophotometer. It shows hydrolysis of the substrate with formula (I) by the joint action of CPU or N of the sample and of CPA.

The delta ODs (ΔOD) measured are compared with the values on a calibration curve which can, for example, be obtained from a sample that is deficient in the CPN or CPU studied, overloaded with this purified enzyme.

The protocol described above constitutes a preferred implementation of the invention. However, several variations can be envisaged, both as regards the sequence in which the different compounds are added, and the nature of said compounds. They are also encompassed by the definition of the present invention.

Thus, for example, it is possible to incorporate the substrate with formula (I) from the start of the method, at the same time as the coagulation activator buffer.

Similarly, the assay can be carried out from two aliquots of the same reaction medium, only one of which is treated with CPA. The ΔOD between these two aliquots is then measured.

When the activator buffer activates coagulation, activation can be carried out using different routes that are known to the skilled person, and used routinely in coagulation tests.

These activation routes are in particular:

the route for activation by the thrombin/thrombomodulin complex. This first possibility constitutes a preferred implementation of the present invention;

the activated factor XI activation route, which in this case replaces thrombin in the activator buffer. To accelerate the reaction, it may be advantageous to add thrombomodulin to the medium;

the venom activation route, in particular snake venoms, also with possible addition of prothrombin and/or thrombomodulin to the medium. Preferred venoms are venoms from the "thrombin-like" venom family such as *Arkistrodon rhodostoma* or *Bathrops atrox* venom, and prothrombin activator venoms such as those from *Notechis scutatus* or *Echis carinatus* (15-18);

the tissue factor activation route, in the presence of phospholipids and calcium (activation of the exogenic route using the Quick time principle);

the contact phase activation route;

the plasmin activation route.

Advantageously, the method of the invention can measure, for the same sample, firstly the activity of the "constitutional" CPN and/or CPU present therein, i.e. the CPN and/or CPU present in the "naturally" active form (i.e. without induction of activation by an activator buffer), and secondly the activity of activatable CPN and/or CPU, i.e. the CPN and/or CPU present in the sample in an inactive form, the activity of which will be induced or generated during the activation process linked to the activator buffer.

To this end, the hydrolyzing activity on a substrate with formula (I) of a sample is compared using the method described above, using the sample either in the presence of activator buffer (detection of the total activity of CPN or CPU in the sample), or in the presence of a physiological buffer without activator (detection of the activity of the constitutional CPN and/or CPU).

The difference (delta OD) between the two measurements gives the activity of the activatable CPN or CPU present in the sample.

In a preferred variation, the present invention concerns a method for assaying activated TAFI in a biological sample, in particular a blood sample, said method using one of the compounds or substrates with formula (I) described above.

The activity of constitutional and/or activatable TAFT is measured by treating the sample as just defined, in the presence and absence of a specific TAFT inhibitor.

The preferred inhibitor is CPI (Carboxypeptidase Inhibitor from Potato Tubers), the use of which, in in vitro and in vivo studies, on the function of TAFT has been widely described in the literature (reference 1). It is now well known to the skilled person that CPI specifically inhibits TAFI without altering the activity of other plasmatic CPs. Within the context of the method of the invention, CPI can be used in a range of concentrations of 0.10 to 0.50 mM (initial concentrations), or 2 to 10 µM expressed as the final concentrations. It is preferably used in a concentration of 7 µM (final concentration) or 0.38 mM (initial concentration).

In accordance with the principle of this preferred variation, the sample is activated by TAFI activation buffer, for example an activation buffer for coagulation by the thrombin/thrombomodulin complex, and treated using the method described above in the presence or in the absence of a TAFI inhibitor.

The difference in coloration of the medium with and without TAFI inhibitor thus allows the enzymatic activity of the activated TAFI (TAFIa) in the sample to be determined.

More precisely, the method of the invention can be carried out using the following protocol: the test sample is divided into 2 aliquots or more if necessary, depending on whether the activity of all of the TAFI contained in the sample is to be determined or whether the distinction between the activity of the constitutional TAFI and that of the activatable TAFI is to be determined.

- a first aliquot containing TAFI inhibitor is activated and treated using the method described above. This will only generate a slight decolorization of the medium, resulting from residual hydrolysis of the substrate with formula (I) by other carboxypeptidases present in the sample;

- a second aliquot is treated in an identical manner, but in the absence of TAFI inhibitor. This results in severe decoloration of the medium, linked to hydrolysis of the substrate with formula (I) by activated TAFI in the sample;

- the difference in coloration ($\Delta OD$) between the first and second aliquot is measured. This is representative of the specific activity of activated TAFI in the sample.

If the distinction is to be made between the specific activity of activatable TAFI and that of constitutional TAFI, a third aliquot of the same sample is used the hydrolysis activity of which is measured on the substrate with formula (I), but in which activation will not have been triggered, by not adding any activator buffer to the medium.

The $\Delta OD$ between these different aliquots can give either the total TAFI activity of the sample, or that of only the constitutional TAFI, and thus that of the activatable TAFI can be deduced.

In a third aspect, the invention concerns a diagnostic kit for assaying a CPN or CPU, said diagnostic kit comprising a substrate with formula (I) as defined above.

Preferably, the diagnostic kit of the present invention is a kit for measuring the TAFI activity in a blood sample.

Said diagnostic kit comprises:
a TAFI activator, in particular a TAFI activator buffer;
carboxypeptidase A;
a substrate with formula (I);
a TAFI inhibitor.

The kit also optionally comprises a protease serine inhibitor.

Each of these components is preferably in the powder form or in the freeze-dried form.

The examples below and the figures illustrate the present invention.

BRIEF DESCRIPTION OF THE DRAWINGS

FIG. 4: Calibration curve for a concentration range obtained from a plasma pool. The calibration was made using the thrombin generation method. The colorimetric assay was made with the chromogenic substrate 4-MTPAFYR.

EXAMPLE 1

Figure 1A:
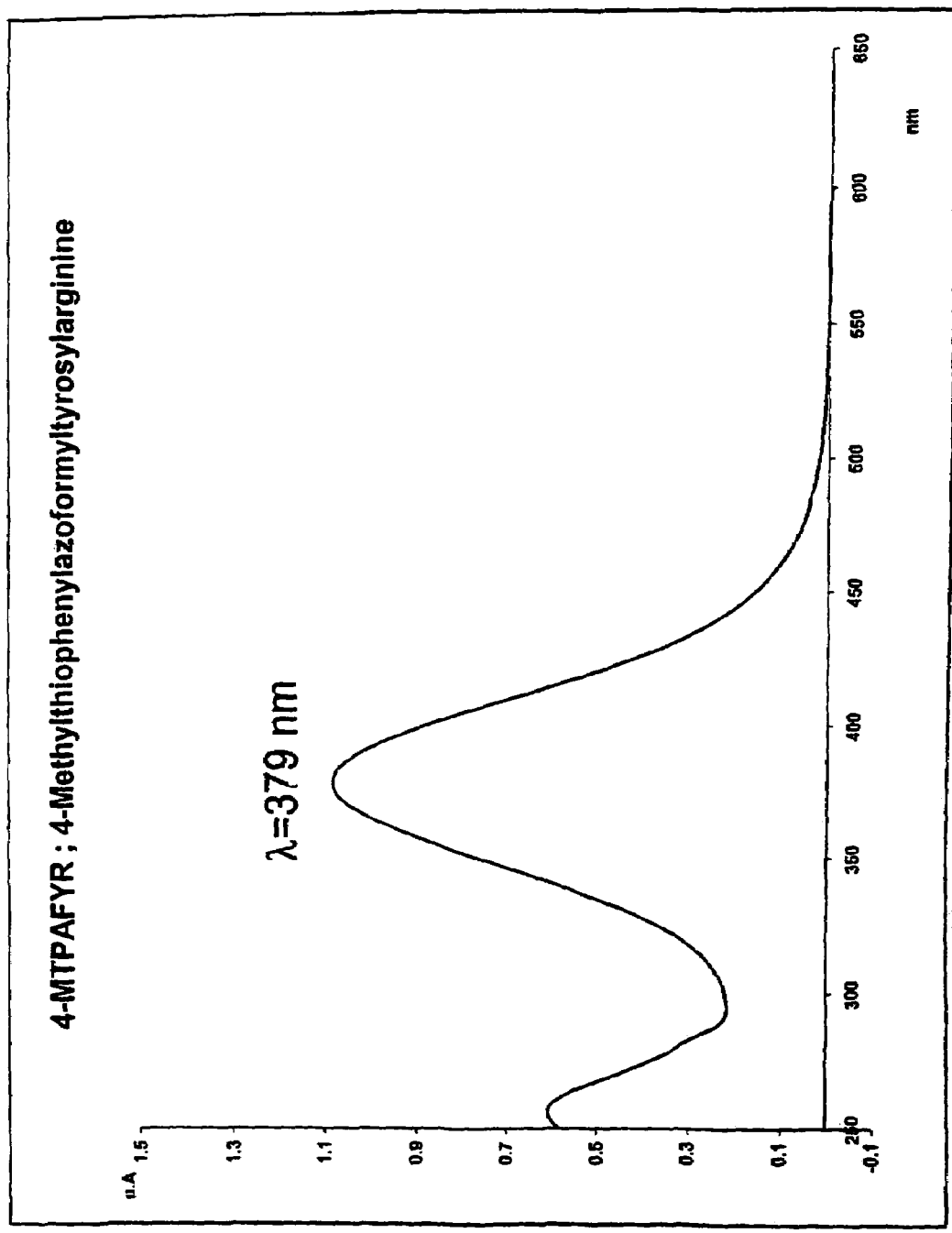
FIG. 1: Absorption spectrum of different synthesized compounds with formula (I), measured with a UV-visible spectrophotometer.
Figure 1B:
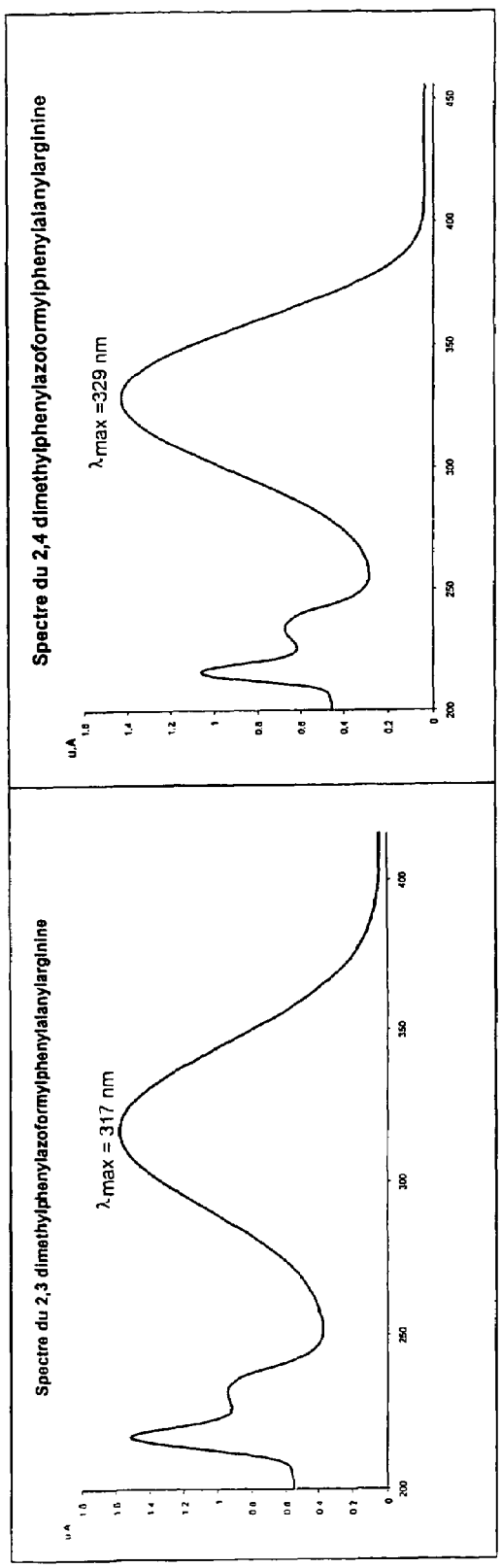
Figure 1B:
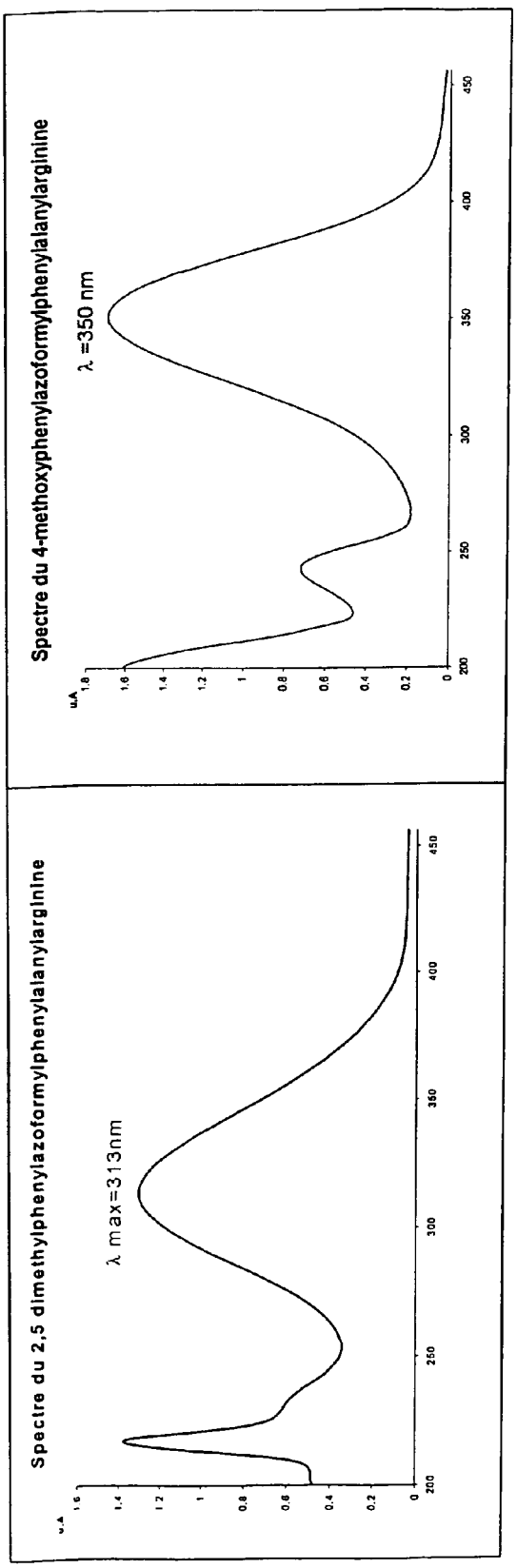
Figure 1C:
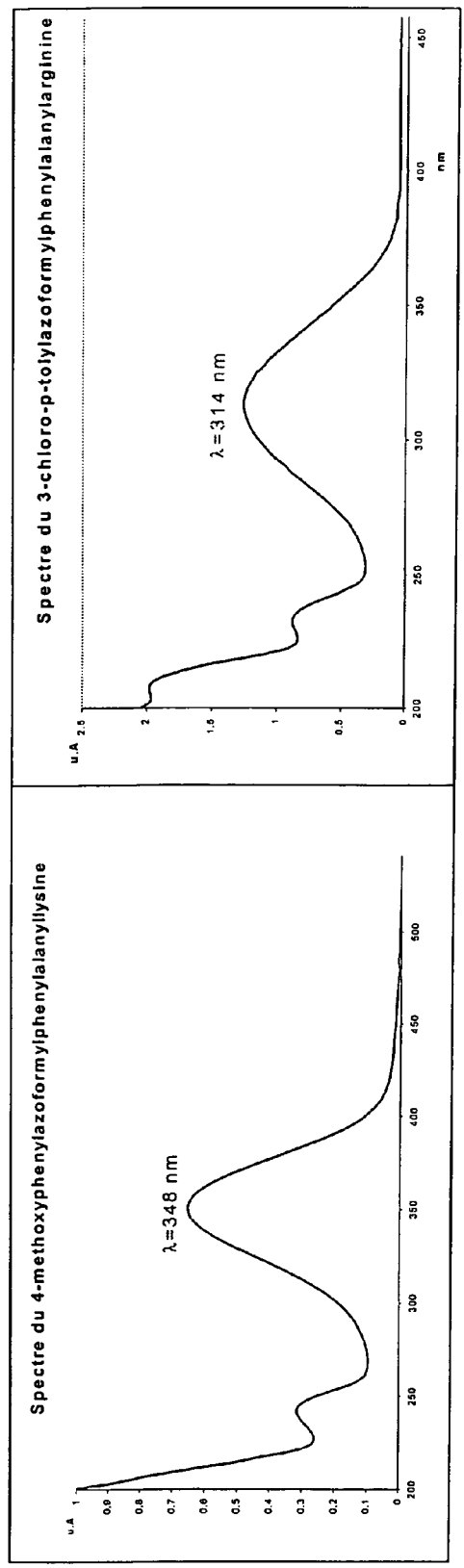
Figure 1C:
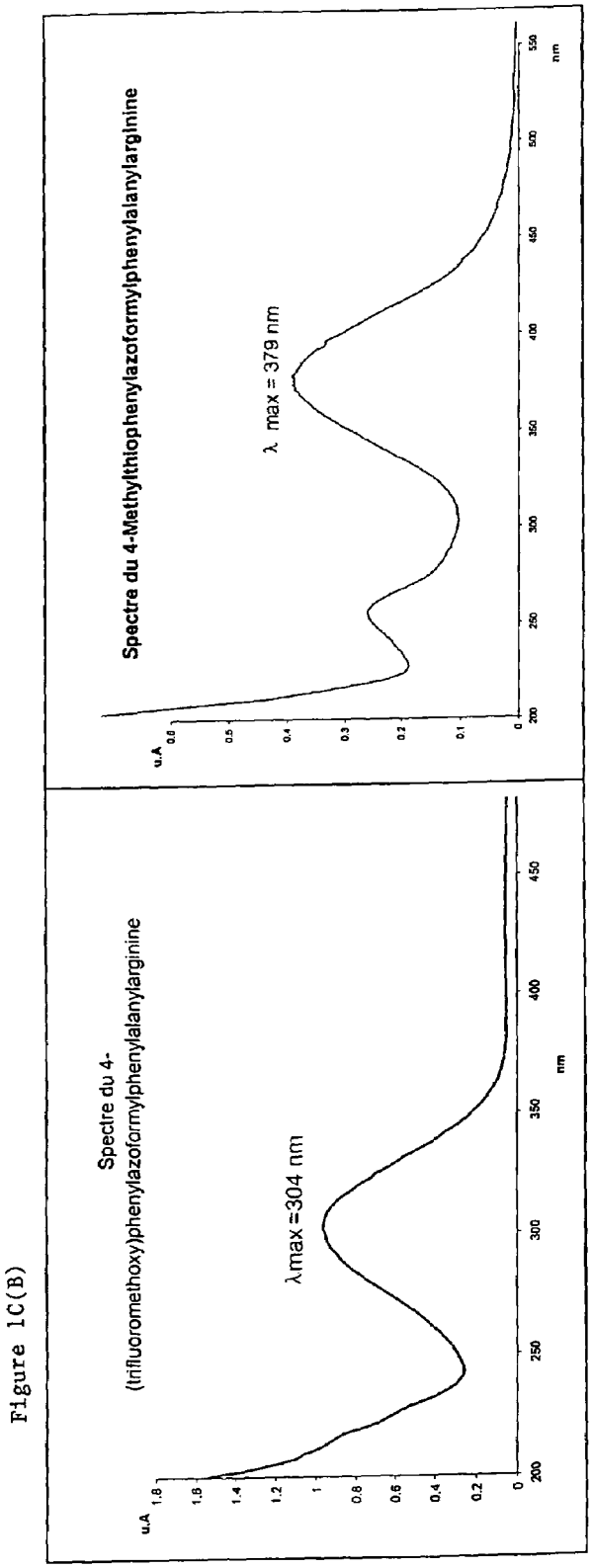

Synthesis of a Group of Azolformyl Compounds in Accordance with the Invention

Table I below indicates the chemical formulae of 8 preferred compounds from compounds with formula (I) of the invention. Their absorption spectra measured with a UV-visible spectrophotometer (UVIKON-KONTRON) are shown in FIG. 1.

We shall detail below the synthesis of one thereof, compound n° 4 (MxPAFFR): The steps described below for this compound are identical for each of the others, except for compound n° 5 (MxPAFFK) for which a supplemental step for deprotecting lysine was necessary (see the reaction scheme and the explanations below).

TABLE 1
| FORMULAE | FORMULES |
|---|---|
| Compound 1: | Composé 1: 2,3 DMPAFFR 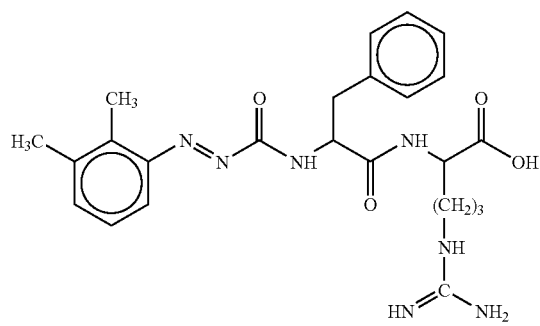 2,3-dimethylphenylazoformylphenylalanylarginine |
| Compound 2: | Composé 2: 2,4 DMPAFFR 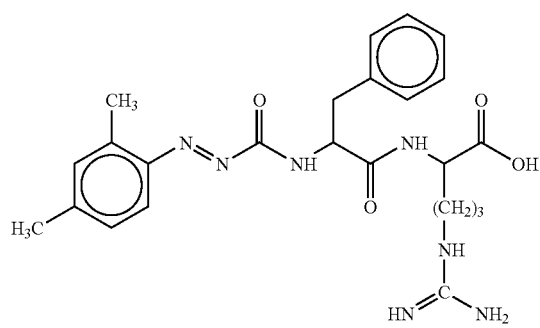 2,4-dimethylphenylazoformylphenylalanylarginine |
| Compound 3: | Composé 3: 2,5 DMPAFFR 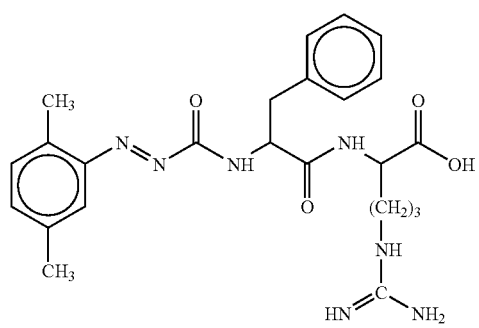 2,5-dimethylphenylazoformylphenylalanylarginine |

TABLE 1-continued
| FORMULAE | FORMULES |
|---|---|
| Compound 4: | Composé 4: MxPAFFR 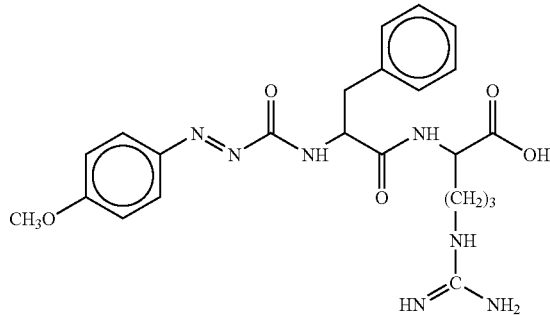 4-methoxyphenylazoformylphenylalanylarginine |
| Compound 5: | Composé 5: MxPAFFK 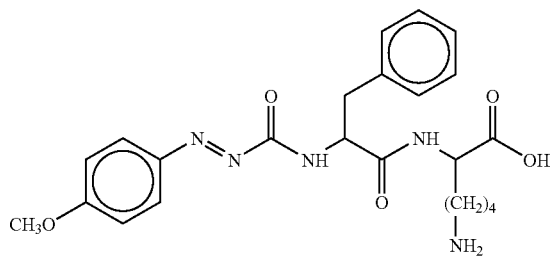 4-methoxyphenylazoformylphenylalanyllysine |
| Compound 6: | Composé 6: CITAFFR 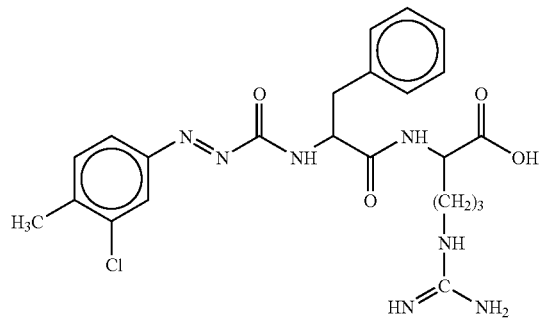 3-chloro-p-tolylazoformylphenylalanylarginine |
| Compound 7: | Composé 7: TFMxPAFFR 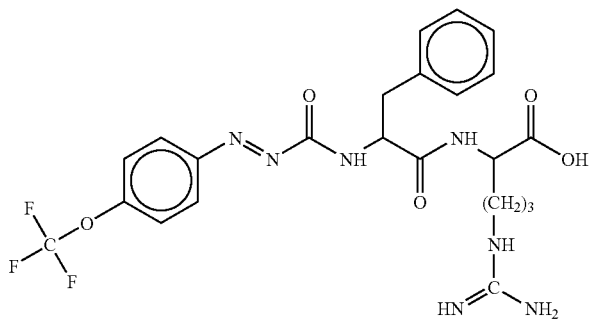 4-(trifluoromethoxy)axoformylphenylalanylarginine |

TABLE 1-continued

| FORMULAE | FORMULES |
|---|---|

Compound 8:

Composé 8:4-MTPAFFR

![Structure of compound 8]

4-Methylthiophenylazoformylphenylalanylarginine

Compound 9:

Composé 9:4-MTPAFYR

![Structure of compound 9]

4-Methylthiophenylazoformyltyrosylarginine

A/ Synthesis of 4methoxyphenylazoformylphenylalanylarginine (compound 4):

Introduction: All of the steps described below were identical for each colorant. Each step was monitored using high performance liquid chromatography and amino acid analysis for the coupling with phenylalanine and arginine.

1$^{st}$ Step: Grignard's Reagent

Reaction scheme:

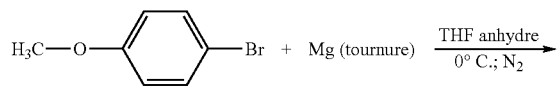

4-bromoanisole        Magnésium

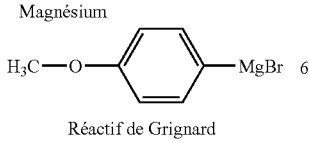

Réactif de Grignard

KEY: Mg (tournure)=Mg (chips), THF anhydre=anhydrous THF: Réactif de Grignard=Grignard's reagent Operating mode: 1 equivalent of 4-bromoanisole and 1 equivalent of magnesium were prepared. The magnesium and 20% by weight of the 4-bromoanisole were introduced into a three-necked flask and taken up in anhydrous tetrahydrofuran (2 ml/mmol) and the assembly was placed under nitrogen. The reaction was initiated by heating the three-necked flask at one point using a blow torch; the reaction mixture turned brown. When the reaction initiated (effervescence on the magnesium surface), it was placed under reflux at 90° C. then the remaining 4-bromoanisole taken up in anhydrous THF (2 ml/mmol) was slowly added. Refluxing was stopped after 1 h. The 4-methoxyphenylmagnesium bromide was used as synthesized for the next step (brown color).

NB: The glassware and magnesium were first oven dried at 120° C. and the other products were dried in a dessicator.

Retention time: Since Grignard's reagent is a very unstable, water-sensitive compound, three characteristic retention times for the degradation products formed during HPLC analysis were obtained:

Retention time 1: 2.68 min;
Retention time 2: 3.32 min;
Retention time 3: 5.38 min

2nd Step: Coupling with di-t-butylazodicarboxylate

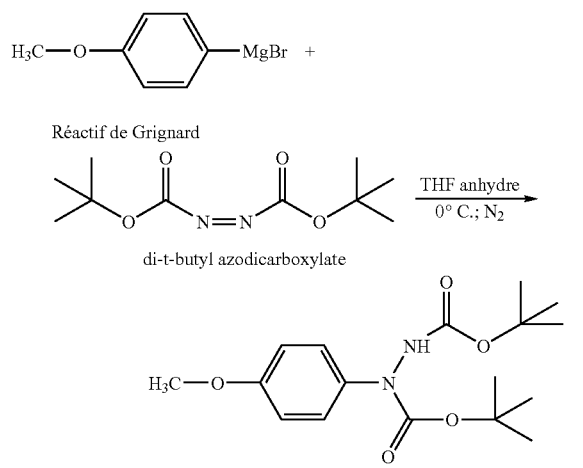

N,N'-bis-(t-butoxycarbonyll)-4-(methoxy)phenylhydrazine

KEY: THF anhydre = anhyrous THF; Réactif de Grignard = Grignard's reagent

Operating mode: 1 equivalent of di-t-butylazodicarboxylate and 1 equivalent of 4-methoxyphenylmagnesium bromide (Grignard's reagent) were taken up in anhydrous THF (2 ml/mmol). Each was cooled to between 0-5° C. The Grignard's reagent was added to the di-t-butylazodicarboxylate. It was stirred for 10 min, 1.02 equivalent of acetic acid was added then it was allowed to return to ambient temperature. Water/ether extraction was carried out. The ether phase was dried and evaporated to dryness. A yellow oil was obtained.

Retention time: 7.85 min.

3rd Step: Deprotection

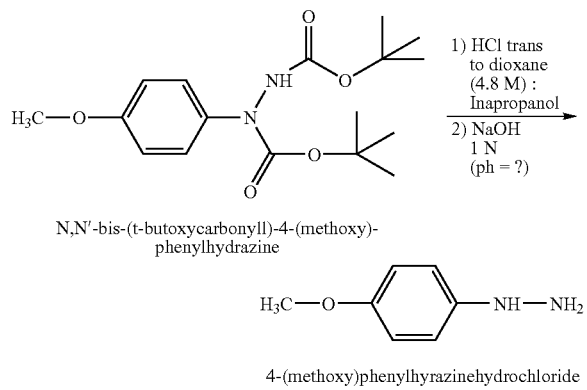

KEY: HCl dans le dioxane (4.8 M) = HCl in dioxane (4.8 M)

Operating mode: 1 equivalent of N,N'-bis-(t-butoxycarbonyl)-4-(methoxy)phenythydrazine was taken up in isopropanol (10.2 ml/mmol) then HCl in 4.8 M in dioxane (2 ml/mmol) was added. It was heated to reflux (80° C.). After 15 min, it was cooled, ether was added (5 ml/mmol). 4-methoxyphenylhydrazinehydrochloride precipitated out. It was filtered and dried. The powder was taken up in water then brought to a pH of 7. Water/dichloromethane extraction was carried out and the dichloromethane was evaporated to dryness. 4-methoxyphenylhydrazine (yellow powder) was obtained and dried.

Retention time: 2.20 min.

4th Step: Coupling with Diphenylcarbonate

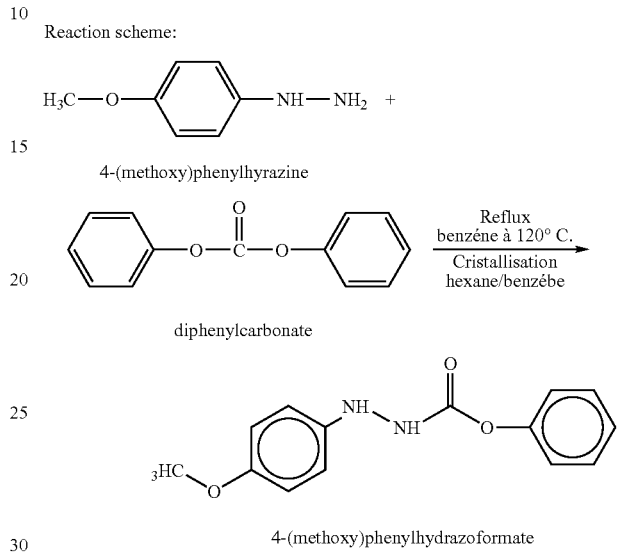

KEY: reflux benzene à 120° C. = benzene reflux at 120° C.; Cristallisation hexane/benzéne = hexane/benzene crystallisation Operating mode: 1.4 equivalent of diphenylcarbonate was taken up in benzene (0.25 ml/mmol) and heated to reflux at 120° C. 1 equivalent of 4-methoxyphenylhydrazine taken up in benzene (0.7 ml/mmol) was slowly added. Reflux was halted after 6 h. The reaction medium was concentrated then hexane/benzene crystallization was carried out (4/1). The whitish crystals were filtered and dried in the dessicator.

Retention time: 6.74 min.

5th Step: Coupling with Phenxyalanine

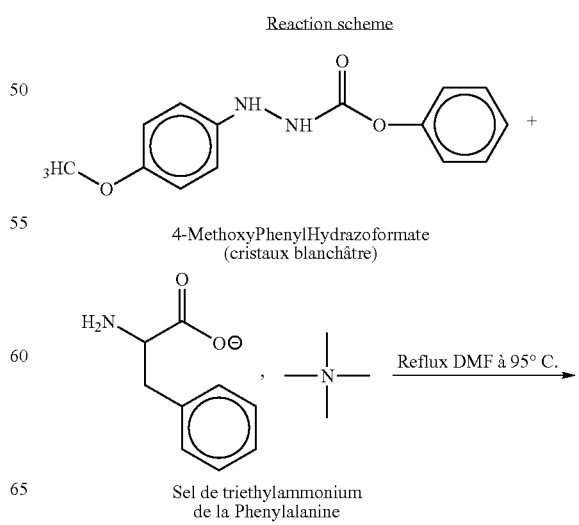

-continued

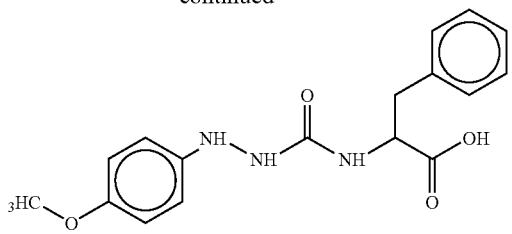

N-(4-MethoxyPhenylHydrazoFormyl)-L-PhenylAlanine
(cristaux blanchâtre)

KEY: (cristaux blanchâtre) = (whitish crystals): Sel de triethylammonium de la Phenylalanine = phenylalanine, triethylammonium salt: Reflux DMF à 95° C. = DMF reflux at 95° C.

Operating mode: 1.2 equivalent of phenylalanine triethylammonium salt taken up in dimethylformamide (3.33 ml/mmol) was heated to reflux (95° C.). 1 equivalent of 4-methoxyphenylhydrazoformate taken up in dimethylformamide (2 ml/mmol) was slowly added. Reflux was stopped after 1 h 30, it was allowed to cool to ambient temperature and concentrated. It was acidified (pH =2). It was purified by chromatography (whitish crystals).

Retention time: 6.12 min.

6$^{th}$ Step: Oxidation; Change from "hydrazo" to "azo" Form

Reaction scheme

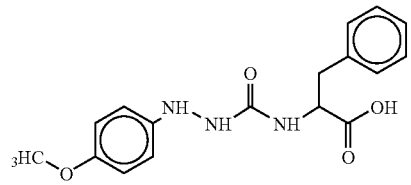

1) Eau:NaOH$_{aq}$ 10%
2) CH$_3$COON$_{aq}$ 10%
3) Métapériodate de sodium

N-(4-MethoxyPhenylHydrazoFormyl)-L-PhenylAlanine
(cristaux blanchâtre)

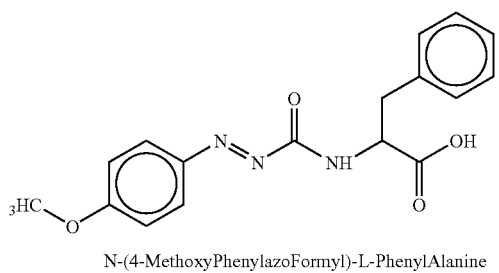

N-(4-MethoxyPhenylazoFormyl)-L-PhenylAlanine
(cristaux orange)

KEY: (cristaux blanchâtre) = (whitish crystals); 1) Eau = 1) Water; 3) Méapériodate de sodium = 3) Sodium metaperiodate; (cristaux orange) = (orange crystals)

Operating mode: 1 equivalent of N-(4-methoxyphenylhydrazoformyl)-L-phenylalanine was taken up in ultra-pure water (20.8 ml/mmol) containing 1 equivalent of sodium hydroxide and 1 equivalent of ammonium acetate. 1 equivalent of sodium metaperiodate taken up in ultra-pure water (4.2 ml/mol) was added. After 20 min, the reaction medium was acidified (pH=2) then purified by chromatography (orange crystals).

Retention time: 6.86 min.

7$^{th}$ Step: Coupling with Arginine

Reaction Scheme

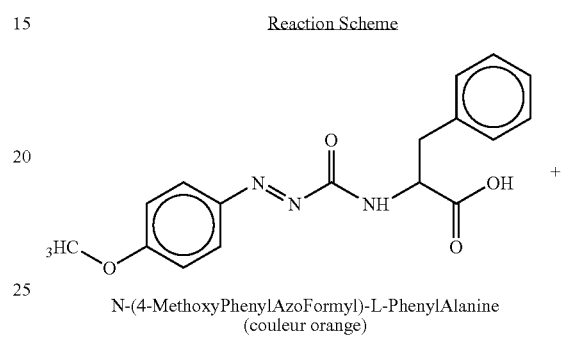

N-(4-MethoxyPhenylAzoFormyl)-L-PhenylAlanine
(couleur orange)

+

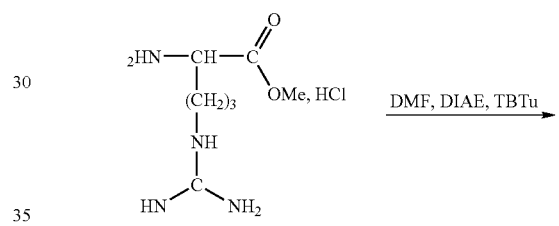

Argininemethylesterhydrochloride

DMF, DIAE, TBTu →

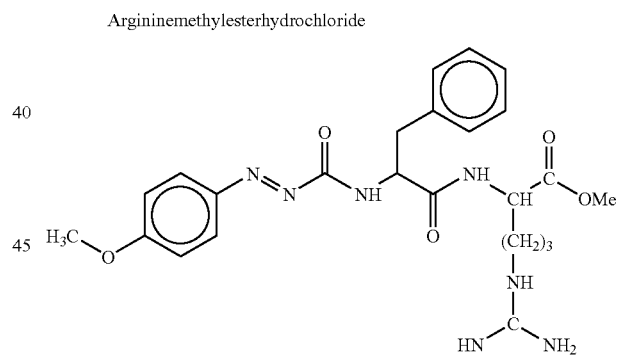

N-(4-MethoxyPhenylAzoFormyl)-L-PhenylAlanylArginineMethylester
(couleur orange)

KEY: (couleur orange) = (orange color)

Operating mode: 1 equivalent of arginine methyl ester hydrochloride was taken up in dimethylformamide (3 ml/mmol). 1.1 equivalent of DIAE (diisopropyl ethylamine), 1 equivalent of N-(4-methoxyphenylazoformyl)-L-phenylalanine then 1.1 equivalent of TBTU (O-benzotriazol-1-yl)-N,N,N', N'-tetramethyluronium tetrafluoroborate) were added. The necessary quantity of DIAE was added to obtain a pH of 7-8. After 5 min, it was evaporated to dryness and purified by chromatography (orange crystals).

Retention time: 6.06 min.

8th Step: Saponification

Reaction Scheme

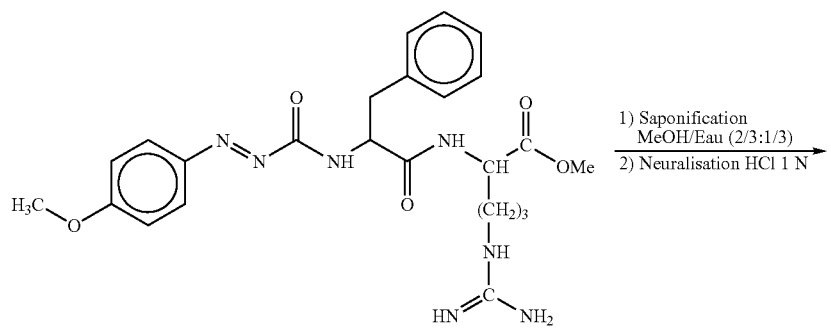

N-(4-MethoxyPhenylAzoFormyl)-L-PhenylAlanineArginineMethylester

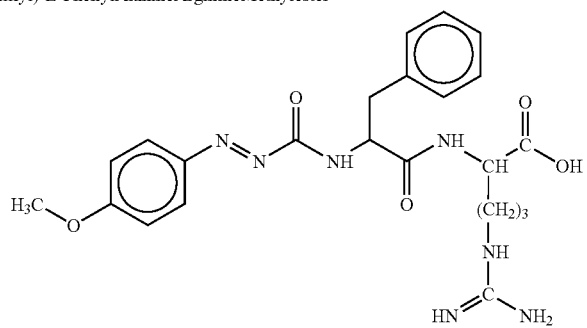

N-(4-MethoxylPhenylAzoFormyl)-L-PhenylAlanineArginine
Anisyl AzoFormylPhenylalanineArginine: AAFFR KEY: MeOH/Eau = MeOH/Water Operating mode: 1 equivalent of N-(4-methoxyphenylazoformyl)L-phenylalanine arginine methyl ester was taken up in a water/methanol mixture (ratio: 1/2; 3 ml/mmol). 3 equivalent of 1 N sodium hydroxide was added. After 1 h, the reactional medium was acidified, concentrated then extracted with water/dichloromethane. The dichloromethane phase was evaporated then dried. N-(4-methoxyphenylazoformyl)-L-phenylalanyl arginine was obtained as an orange powder.

Retention time: 5.5 min.

Figure 2:
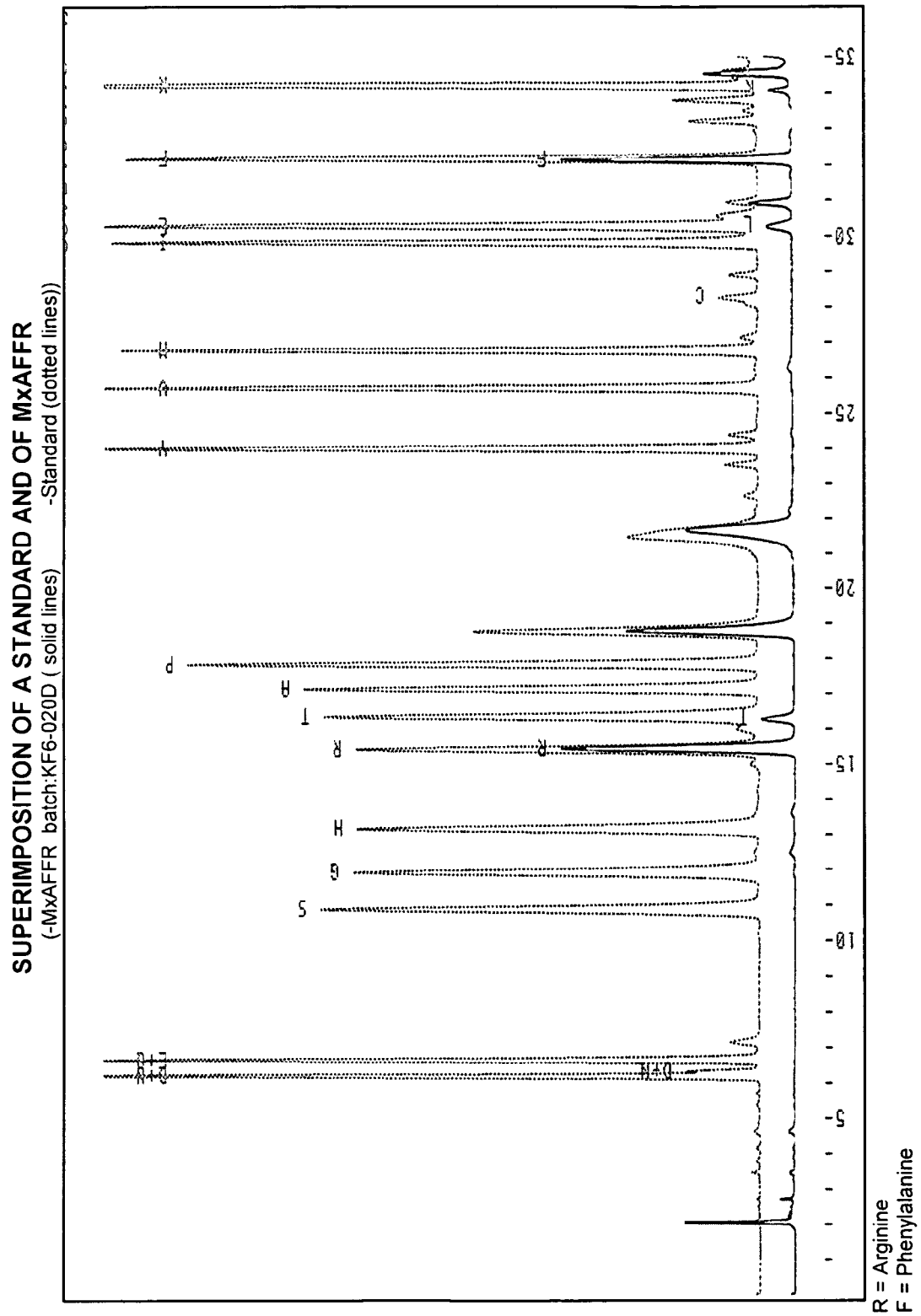
FIG. 2: AAFFR analysis carried out by acid hydrolysis.

Amino acid analysis of the final product was carried out after acid hydrolysis to check the sequence homogeneity. The results of this analysis are shown in the chromatogram in FIG. 2.

Analytical Conditions:
HPLC AAA line: PITC (phenylisocyanate) precolumn derivatization;
C18 column; 100A; 5μ; 250×4.6 mm;
Detection at 254 nm; flow rate=1 ml/min;
Eluents:
  A: pH 5.74 acetate buffer;
  B: 70% $CH_3CN$, 30% AcONa buffer; 32 mM; pH=6.10;
  C: $CH_3CN$ The synthesis protocols for the other compounds are based on the same steps as those described above. They are summarized in the reaction schemes below.

The retention times obtained at each step of the synthesis of said compounds are shown in Table II below:

TABLE II

Retention times obtained with HPLC in each step for the other synthesized colorants

| Step | 2,3DMPAFFR | 2,4DMPAFFR | 2,5DMPAFFR | MxAPFFR | MxPAFFK | CITAFFR | TFMxPAFFR |
|---|---|---|---|---|---|---|---|
| 1 | / | / | / | / | / | / | / |
| 2 | 9.12 min | 9.18 min | 9.15 min | 7.85 min | 7.85 min | 9.25 min | 9.26 min |
| 3 | 3.59 min | 3.81 min | 3.73 min | 2.20 min | 2.20 min | 3.93 min | 3.94 min |
| 4 | 7.87 min | 7.96 min | 7.82 min | 6.74 min | 6.74 min | 8.06 min | 7.92 min |
| 5 | 7.04 min | 7.13 min | 7.11 min | 6.12 min | 6.12 min | 7.51 min | 7.45 min |
| 6 | 7.82 min | 7.88 min | 7.90 min | 6.86 min | 6.86 min | 7.85 min | 7.79 min |
| 7 | 7.10 min | 7.02 min | 7.10 min | 6.06 min | 9.84 min | 7.13 min | 7.08 min |
| 8 | 6.55 min | 6.54 min | 6.62 min | 5.50 min | 9.23 min | 6.71 min | 6.65 min |

Analytical Conditions:
   C18 Column; 5μ; 100×4.6 mm;
   Detection at 254 nm; flow rate=1 ml/min;
   Gradient: 0' 10% B; 10' 90% B
   With A: water with 1% trifluoroacetic acid
      B: acetonitrile with 0.1% trifluoroacetic acid.

B/ Synthesis of 2,3-dimethylphenylazoformylphenylalanylarginine (compound 1):

$1^{st}$ Step: Grignard's Reagent

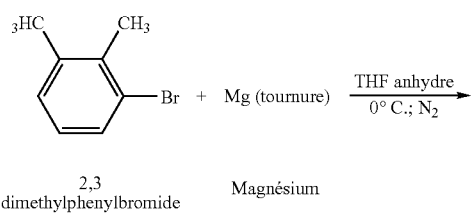

2,3 dimethylphenylbromide  Magnésium

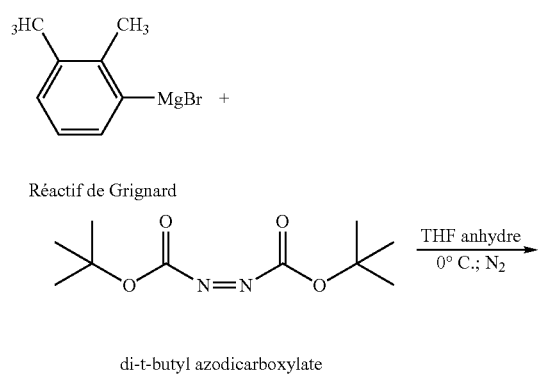

Réactif de Grignard

KEY: Mg (tournure) = Mg (chips); THF anhydre = anhydrous THF; Réactif de Grignard = Grignard's reagent $2^{nd}$ Step: Coupling with di-t-butylazodicarboxylate Réactif de Grignard di-t-butyl azodicarboxylate N,N'-bis-(t-butoxycarbonyll)-2,3-(dimethyl)phenylhydrazine KEY: THF anhydre = anhydrous THF; Réactif de Grignard = Grignard's reagent $3^{rd}$ Step: Deprotection

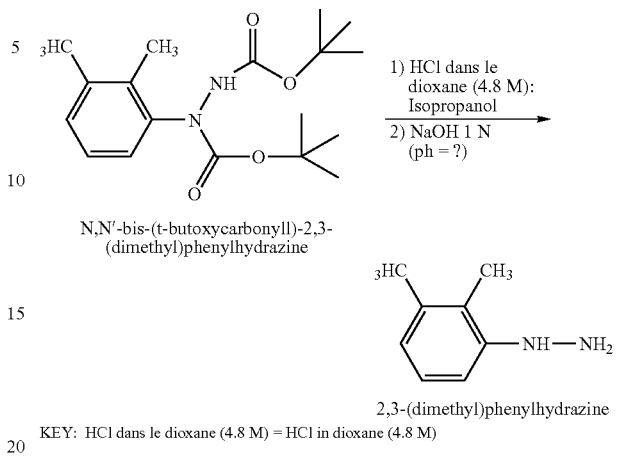

N,N'-bis-(t-butoxycarbonyll)-2,3-(dimethyl)phenylhydrazine 2,3-(dimethyl)phenylhydrazine KEY: HCl dans le dioxane (4.8 M) = HCl in dioxane (4.8 M)

$4^{th}$ Step: Coupling with Diphenylcarbonate 2,3-(dimethyl)phenylhydrazine

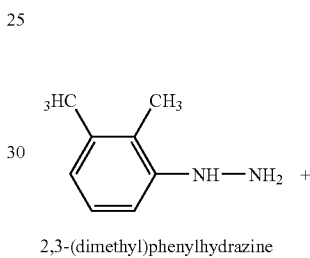

diphenylcarbonate

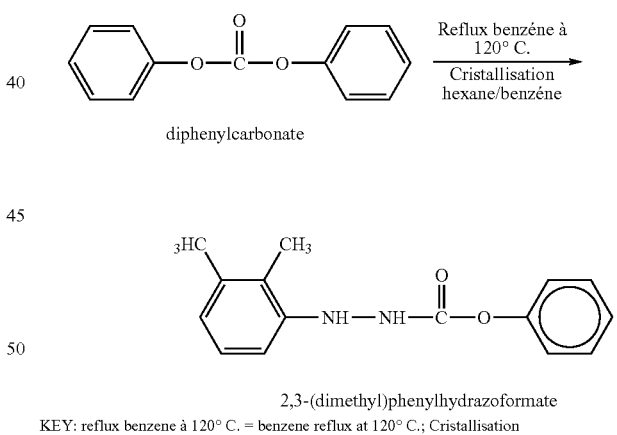

2,3-(dimethyl)phenylhydrazoformate

KEY: reflux benzene à 120° C. = benzene reflux at 120° C.; Cristallisation hexane/benzéne = hexane/benzene crystallization $5^{th}$ Step: Coupling with Phenylalanine

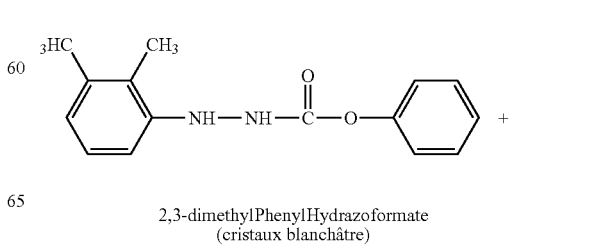

2,3-dimethylPhenylHydrazoformate
(cristaux blanchâtre)

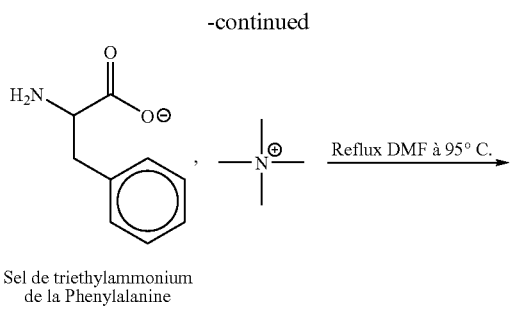

Sel de triethylammonium
de la Phenylalanine

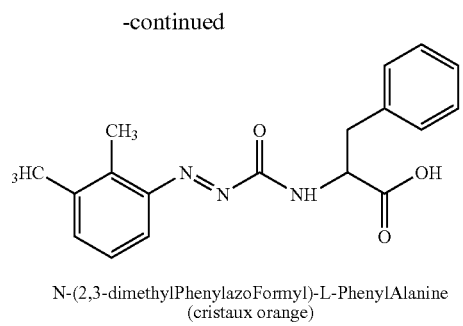

N-(2,3-dimethylPhenylazoFormyl)-L-PhenylAlanine
(cristaux orange)

KEY: (cristaux blanchâtre) = (whitish crystals); 1) Eau = 1) Water; 3) Métapériodate de sodium = 3) Sodium metaperiodate; (cristaux orange) = (orange crystals)

7<sup>th</sup> step: Coupling with Arginine

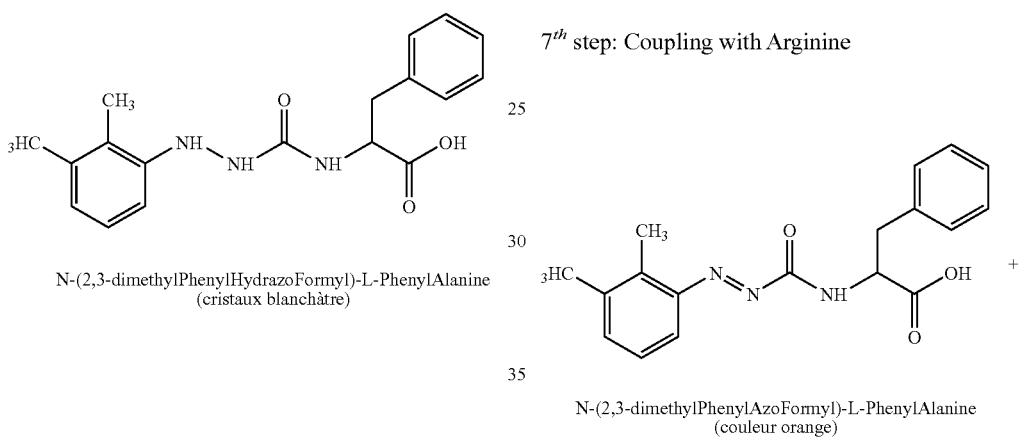

N-(2,3-dimethylPhenylHydrazoFormyl)-L-PhenylAlanine
(cristaux blanchâtre)

N-(2,3-dimethylPhenylAzoFormyl)-L-PhenylAlanine
(couleur orange)

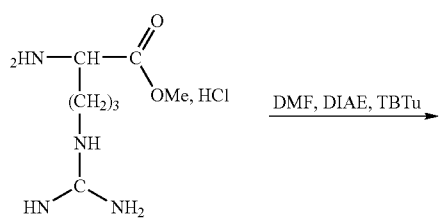

Argininemethylesterhydrochloride

KEY: (cristaux blanchâtre) = (whitish crystals); Sel de triethylammonium de la Phenylalanine = phenylalanine, triethylammonium salt; Reflux DMF à 95° C. = DMF reflux at 95° C.

6<sup>th</sup> Step: Oxidation; Change from "hydrazo" to "azo" Form

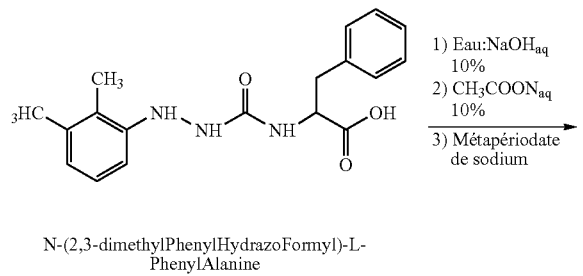

N-(2,3-dimethylPhenylHydrazoFormyl)-L-
PhenylAlanine
(cristaux blanchâtre)

N-(2,3-dimethylPhenylAzoFormyl)-L-PhenylAlanylArginineMethylester
(couleur orange)

KEY: (couleur orange) = (orange color)

8th Step: Saponification

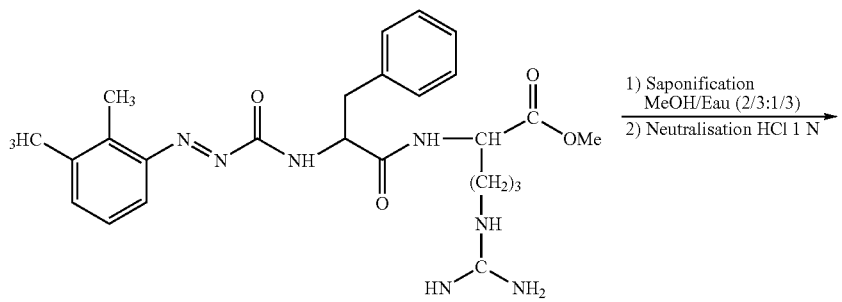

N-(2,3-dimethylPhenylAzoFormyl)-L-PhenylAlanylArginineMethylester
(couleur orange)

1) Saponification MeOH/Eau (2/3:1/3)
2) Neutralisation HCl 1 N

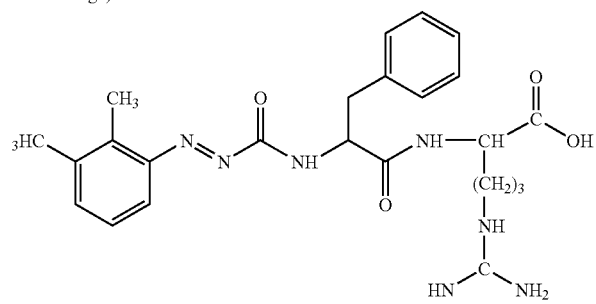

N-(2,3-dimethylPhenylAzoFormyl)-L-PhenylAlanineArginine

KEY: MeOH/Eau = MeOH/Water; (couleur orange) = (orange color)

C/Synthesis of 2,4-dimethylphenylazoformylphenylalanylarginine (compound 2):

1st Step: Grignard's Reagent

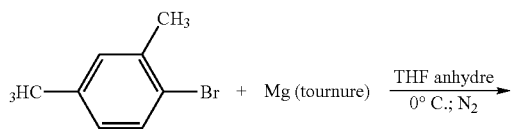

2,3 dimethylphenylbromide    Magnésium

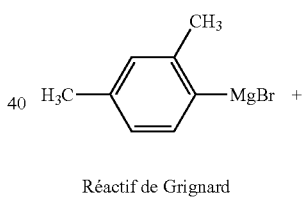

Réactif de Grignard

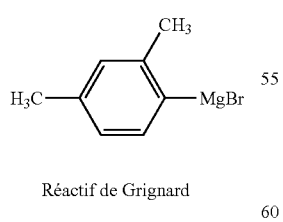

Réactif de Grignard

KEY: Mg (tournure) = Mg (chips); THF anhydre = anhydrous THF; Réactif de Grignard = Grignard's reagent 2nd step: Coupling with di-t-butylazodicarboxylate

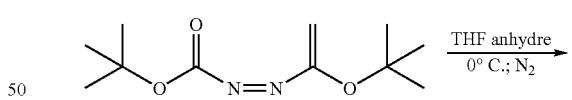

di-t-butyl azodicarboxylate

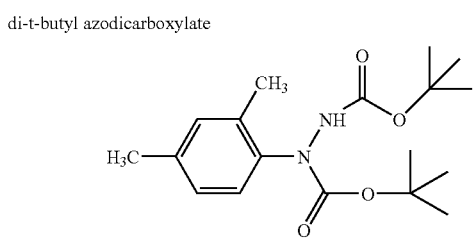

N,N'-bis-(t-butoxycarbonyl)-2,4-(dimethyl)phenylhydrazine

KEY: THF anhydre = anhydrous THF; Réactif de Grignard = Grignard's reagent

3rd step: Deprotection

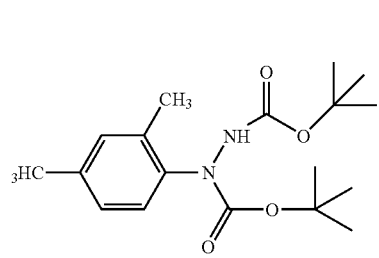

N,N'-bis-(t-butoxycarbonyll)-2,4-(dimethyl)phenylhydrazine

1) HCl dans le dioxane (4.8 M): Isopropanol
2) NaOH 1 N (ph = ?)

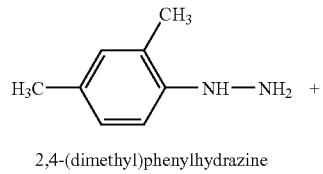

2,4-(dimethyl)phenylhydrazine

KEY: HCl dans le dioxane (4.8 M) = HCl in dioxane (4.8 M)

4th step: Coupling with Diphenylcarbonate

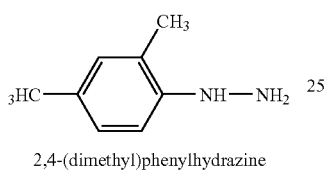

2,4-(dimethyl)phenylhydrazine

+

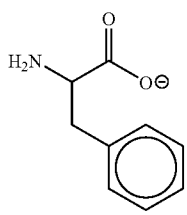

diphenylcarbonate

Reflux benzéne à 120° C.
Cristallisation hexane/benzéne

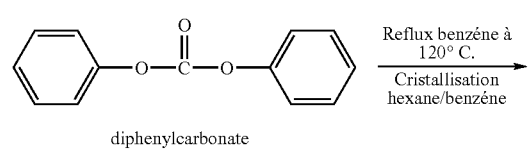

2,4-(dimethyl)phenylhydrazoformate

KEY: reflux benzene à 120° C. = benzene reflux at 120° C.; Cristallisation hexane/benzéne = hexane/benzene crystallization 5th step: Coupling with Phenylalanine

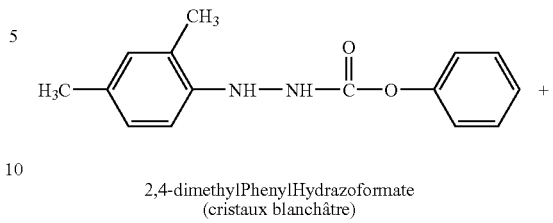

2,4-dimethylPhenylHydrazoformate (cristaux blanchâtre)

+

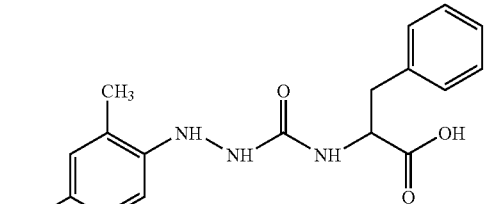

Sel de triethylammonium de la Phenylalanine

Reflux DMF à 95° C.

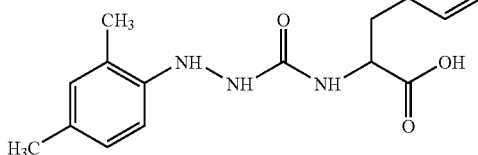

N-(2,4-dimethylPhenylHydrazoFormyl)-L-PhenylAlanine (cristaux blanchâtre)

KEY: (cristaux blanchâtre) = (whitish crystals); Sel de triethylammonium de la Phenylalanine = phenylalanine, triethylammonium salt; Reflux DMF à 95° C. = DMF reflux at 95° C.

6th step: Oxidation: Change from "hydrazo" to "azo" Form

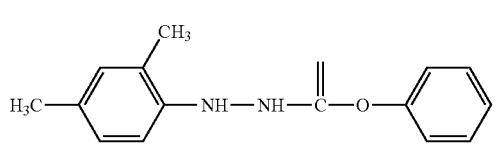

N-(2,4-dimethylPhenylHydrazoFormyl)-L-PhenylAlanine (cristaux blanchâtre)

1) Eau:NaOH$_{aq}$ 10%
2) CH$_3$COON$_{aq}$ 10%
3) Métapériodate de sodium

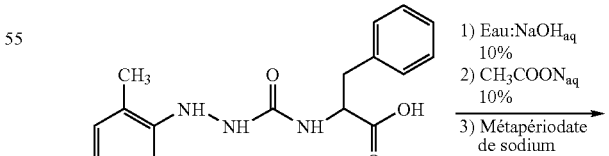

-continued

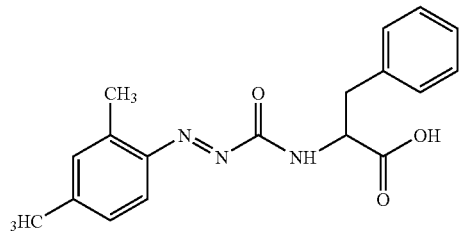

N-(2,4-dimethylPhenylazoFormyl)-L-PhenylAlanine
(cristaux orange)

KEY: (cristaux blanchâtre) = (whitish crystals); 1) Eau = 1) Water; 3) Métapériodate de sodium = 3) Sodium metaperiodate; (cristaux orange) = (orange crystals)

7<sup>th</sup> step: Coupling with Arginine

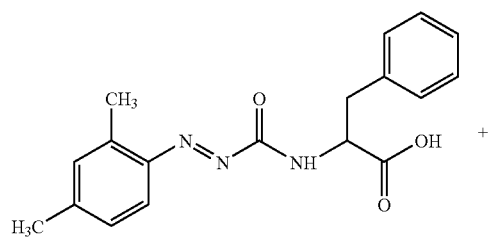

N-(2,4-dimethylPhenylAzoFormyl)-L-PhenylAlanine
(couleur orange)

+

-continued

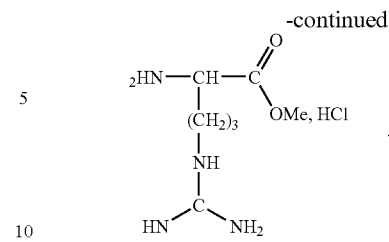

Argininemethylesterhydrochloride

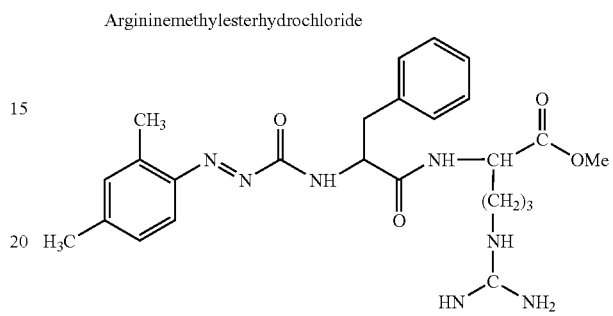

N-(2,4-dimethylPhenylAzoFormyl)-L-PhenylAlanylArginineMethylester
(couleur orange)

KEY: (couleur orange) = (orange color)

8<sup>th</sup> step: Saponification

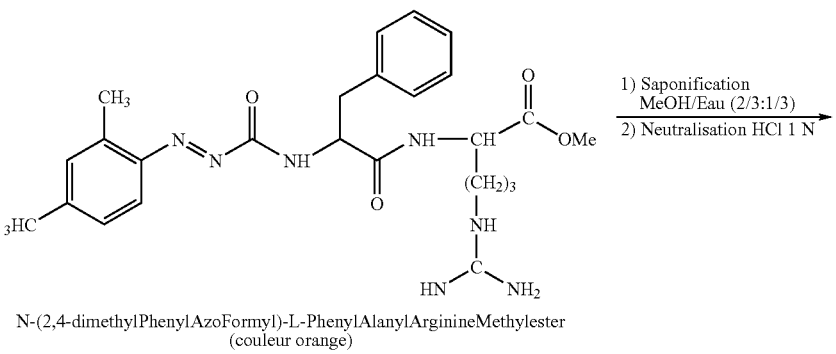

N-(2,4-dimethylPhenylAzoFormyl)-L-PhenylAlanylArginineMethylester
(couleur orange)

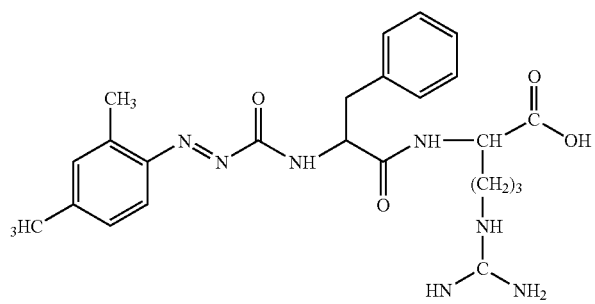

N-(2,4-dimethylPhenylAzoFormyl)-L-PhenylAlanineArginine

KEY: MeOH/Eau = MeOH/Water; (couleur orange) = (orange color)

D/Synthesis of 2,5-dimethylphenylazoformylphenylalanylarginine (compound 3):

1st Step: Grignard's Reagent

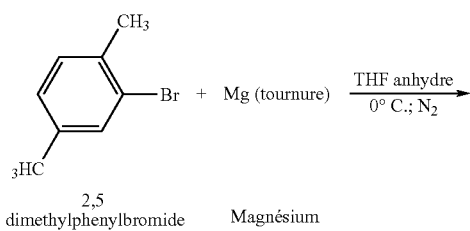

2,5 dimethylphenylbromide    Magnésium

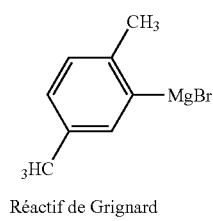

Réactif de Grignard

KEY: Mg (tournure) = Mg (chips); THF anhydre = anhydrous THF; Réactif de Grignard = Grignard's reagent 2nd Step: Coupling with di-t-butylazodicarboxylate

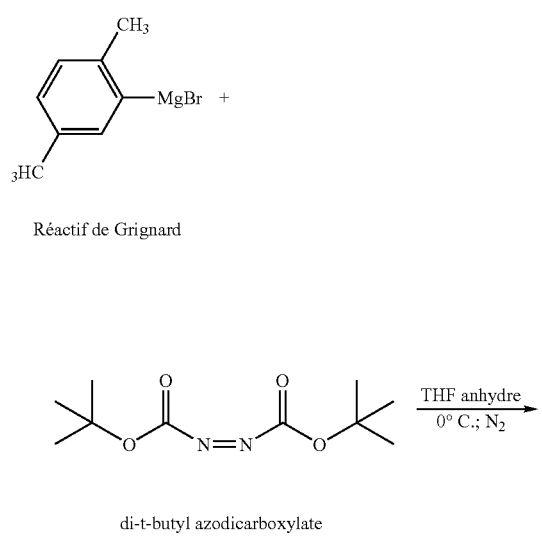

di-t-butyl azodicarboxylate

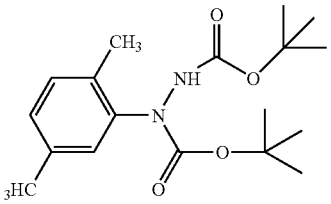

N,N′-bis-(t-butoxycarbonyll)-2,5-(dimethyl)phenylhydrazine

KEY: THF anhydre = anhydrous THF; Réactif de Grignard = Grignard's reagent

3rd Step: Deprotection

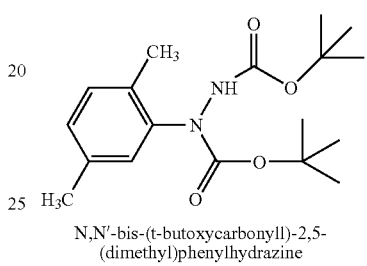

N,N′-bis-(t-butoxycarbonyll)-2,5-(dimethyl)phenylhydrazine

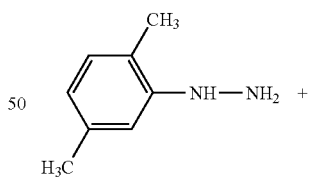

2,5-(dimethyl)phenylhydrazine

KEY: HCl dans le dioxane (4.8 M) = HCl in dioxane 4.8 M

4th Step: Coupling with Diphenylcarbonate

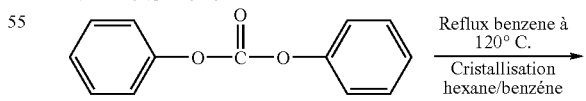

2,5-(dimethyl)phenylhydrazine diphenylcarbonate

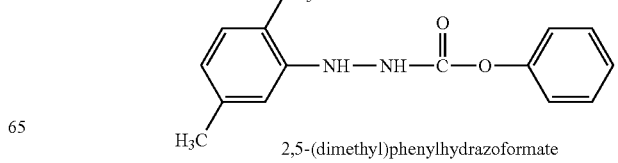

2,5-(dimethyl)phenylhydrazoformate

-continued

KEY: reflux benzene à 120° C. = benzene reflux at 120° C.; Cristallisation hexane/benzéne = hexane/benzene crystallization 5th step: Coupling with Phenylalanine

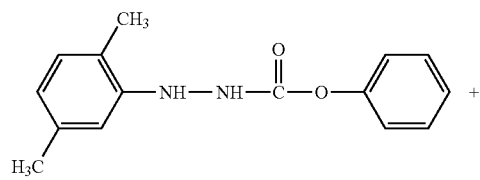

2,5-dimethylPhenylHydrazoformate
(cristaux blanchâtre)

+

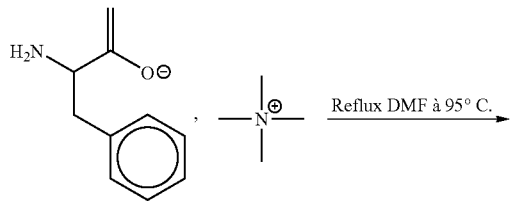

Sel de triethylammonium
de la Phenylalanine

Reflux DMF à 95° C.

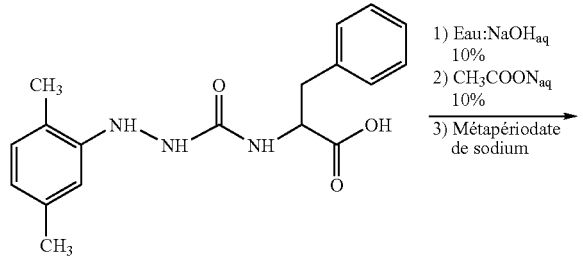

N-(2,5-dimethylPhenylHydrazoFormyl)-L-PhenylAlanine
(cristaux blanchâtre)

KEY: (cristaux blanchâtre) = (whitish crystals); Sel de triethylammonium de la Phenylalanine = phenylalanine, triethylammonium salt; Reflux DMF à 95° C. = DMF reflux at 95° C.

6th Step: Oxidation; Change from "hydrazo" to "azo" Form

1) Eau:NaOH$_{aq}$ 10%
2) CH$_3$COON$_{aq}$ 10%
3) Métapériodate de sodium

N-(2,5-dimethylPhenylHydrazoFormyl)-L-PhenylAlanine
(cristaux blanchâtre)

-continued

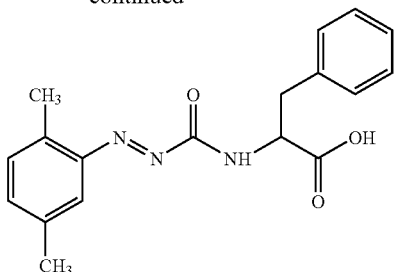

N-(2,5-dimethylPhenylazoFormyl)-L-PhenylAlanine
(cristaux orange)

KEY: (cristaux blanchâtre) = (whitish crystals); 1) Eau = 1) Water; 3) Métapériodate de sodium = 3) Sodium metaperiodate; (cristaux orange) = (orange crystals)

7th Step: Coupling with Arginine

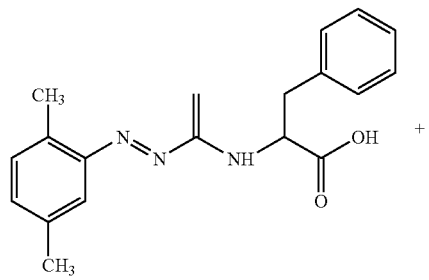

N-(2,5-dimethylPhenylAzoFormyl)-L-PhenylAlanine
(couleur orange)

+

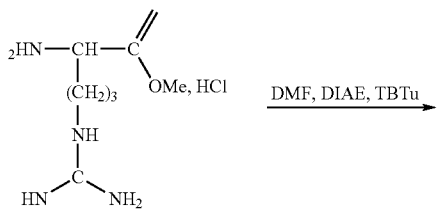

Argininemethylesterhydrochloride

DMF, DIAE, TBTu

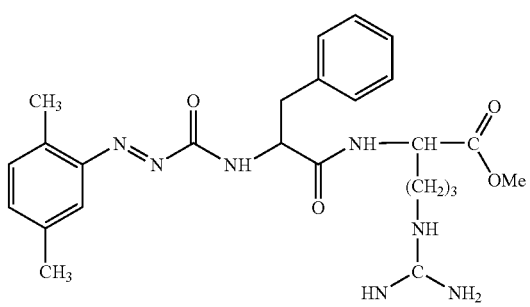

N-(2,5-dimethylPhenylAzoFormyl)-L-PhenylAlanyl-ArginineMethylester
(couleur orange)

KEY: (couleur orange) = (orange color)

8th Step: Saponification

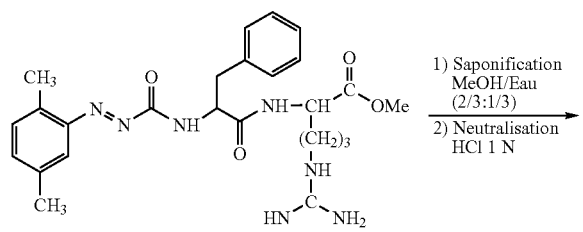

N-(2,4-dimethylPhenylAzoFormyl)-L-PhenylAlanylArginineMethylester
(couleur orange)

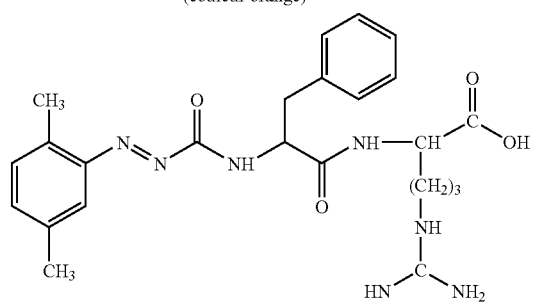

N-(2,4-dimethylPhenylAzoFormyl)-L-PhenylAlanineArginine
KEY: MeOH/Eau = MeOH/Water; (couleur orange) = (orange color)

E/ Synthesis of 4-metboxyphenylazoformylphenylalanyllysine:

1st Step: Grignard's Reagent

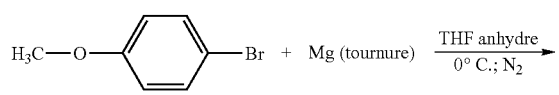

4-bromoanisole    Magnésium

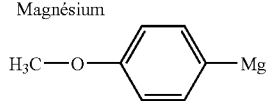

Réactif de Grignard
KEY: Mg (tournure) = Mg (chips); THF anhydre = anhydrous THF; Réactif de Grignard = Grignard's reagent 2nd Step: Coupling with di-t-butylazodicarboxylate

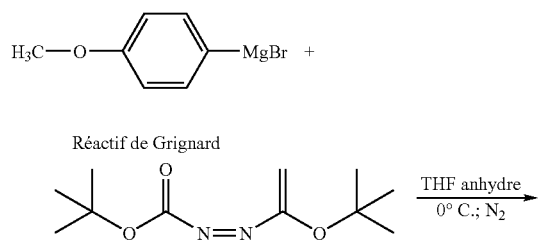

di-t-butyl azodicarboxylate

-continued

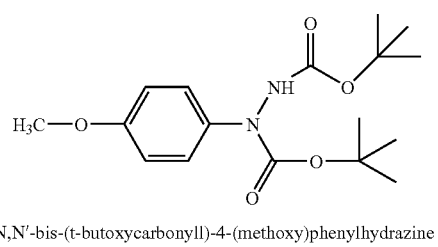

N,N'-bis-(t-butoxycarbonyll)-4-(methoxy)phenylhydrazine
KEY: THF anhydre = anhydrous THF; Réactif de Grignard = Grignard's reagent 3rd Step: Deprotection

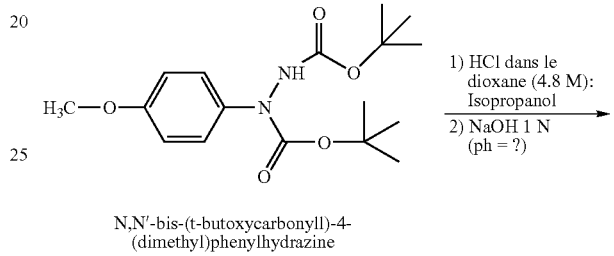

N,N'-bis-(t-butoxycarbonyll)-4-(dimethyl)phenylhydrazine

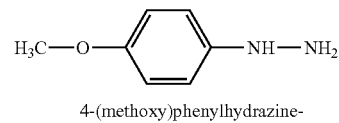

4-(methoxy)phenylhydrazine-hydrochloride

KEY: HCl dans le dioxane (4.8 M) = HCl in dioxane (4.8 M)

4th step: Coupling with Diphenylcarbonate

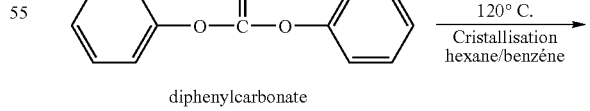

4-(methoxy)phenylhydrazine

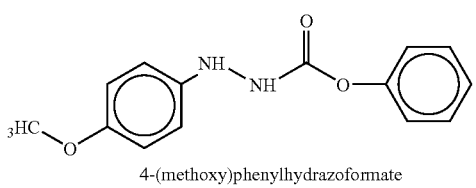

diphenylcarbonate 4-(methoxy)phenylhydrazoformate

-continued

KEY: reflux benzéne à 120° C. = benzene reflux at 120° C.; Cristallisation hexane/benzéne = hexane/benzene crystallization

5th Step: Coupling with Phenylalanine

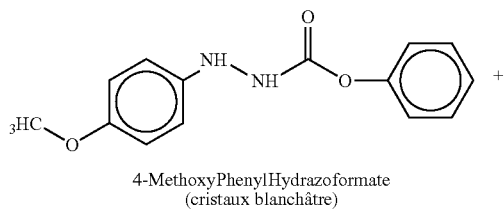

4-MethoxyPhenylHydrazoformate
(cristaux blanchâtre)

+

H₂N—CH(CH₂Ph)—COO⁻ , (CH₃)₃NH⁺ —Reflux DMF à 95° C.→

Sel de triethylammonium
de la Phenylalanine

-continued

KEY: (cristaux blanchâtre) = (whitish crystals); Sel de triethylammonium de la Phenylalanine = phenylalanine, triethylammonium salt; Reflux DMF à 95° C. = DMF reflux at 95° C.

6th Step: Oxidation; Change from "hydrazo" to "azo" Form

[Structure: 3HCO-C₆H₄-NH-NH-C(O)-NH-C(CH₂Ph)=C(OH)]

1) Eau:NaOH_aq 10%
2) CH₃COONa_aq 10%
3) Métapériodate de sodium
→

N-(4-MethoxyPhenylHydrazoFormyl)-L-PhenylAlanine
(cristaux blanchâtre)

[Structure: 3HCO-C₆H₄-N=N-C(O)-NH-CH(CH₂Ph)-COOH]

N-(4-MethoxyPhenylazoFormyl)-L-PhenylAlanine
(cristaux orange)

KEY: (cristaux blanchâtre) = (whitish crystals); 1) Eau = 1) Water; 3) Métapériodate de sodium = 3) Sodium metaperiodate; (cristaux orange) = (orange crystals)

7th Step: Coupling with Lysine

[Structure: 3HCO-C₆H₄-NH-NH-C(O)-NH-CH(CH₂Ph)-COOH with C=O]

N-(4-MethoxyPhenylHydrazoFormyl)-L-PhenylAlanine
(cristaux blanchâtre)

[Structure: 3HCO-C₆H₄-N=N-C(O)-NH-CH(CH₂Ph)-COOH with C=O]

+

N-(4-MethoxyPhenylAzoFormyl)-L-PhenylAlanine
(couleur orange)

8th Step: Saponification

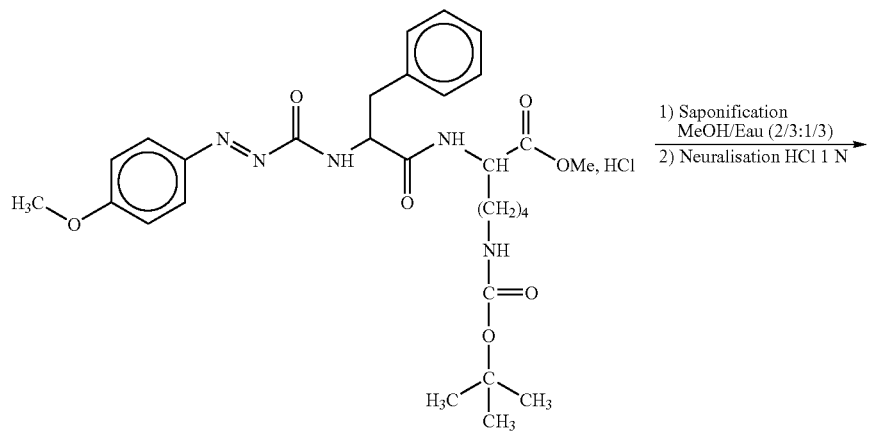

N-(4-MethoxyPhenylAzoFormyl)-L-PhenylAlanylLysine(Boc)Methylester
(couleur orange)

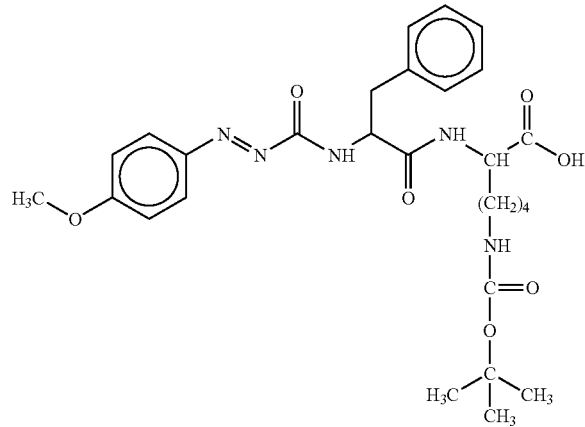

N-(4-MethoxylPhenylAzoFormyl)-L-PhenylAlanineLysine(Boc)
KEY: MeOH/Eau = MeOH/Water; (couleur orange) = (orange color)

9th Step: Deprotection

This particular compound required a supplemental step to deprotect the lysine side chain (ε-boc: N-ε-tertiobutoxycarbonyl).

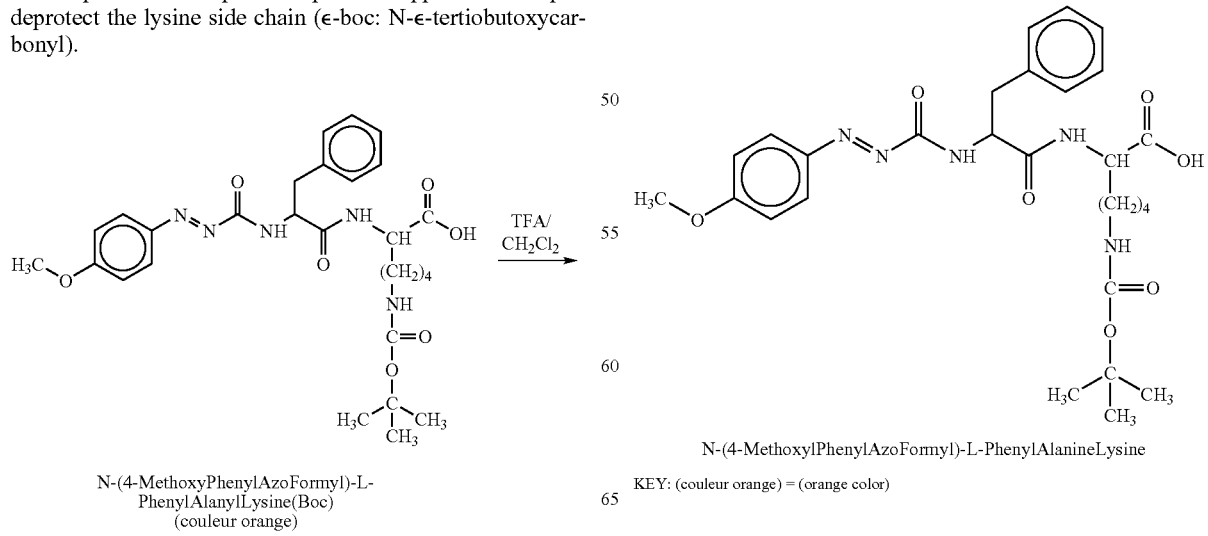

N-(4-MethoxyPhenylAzoFormyl)-L-
PhenylAlanylLysine(Boc)
(couleur orange)

N-(4-MethoxylPhenylAzoFormyl)-L-PhenylAlanineLysine

KEY: (couleur orange) = (orange color)

Operating mode: 1 equivalent of N-(4-methoxyphenylazo-formyl)-L-phenylalanyl-L-lysine (ε-Boc) was taken up in dichloromethane (3 ml/mmol) in a flask. Stirring was commenced. A dropping funnel containing trifluoroacetic acid (3 ml/mmol) was connected. It was added slowly (dropwise). After 15 min, the reaction medium was concentrated and purified by high performance liquid chromatography. In the end, an orange powder was obtained.

F/Synthesis of 3-chloro-p-tolylazoformylphenylalanylarginine (compound 6):

1$^{st}$ Step: Grignard's Reagent

Reaction scheme

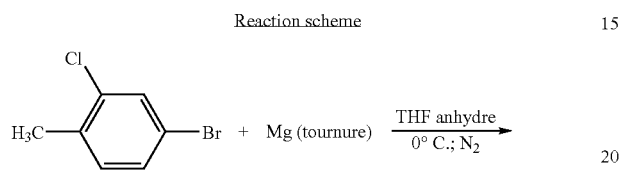

3-chloro-4-bromidetulene    Magnésium

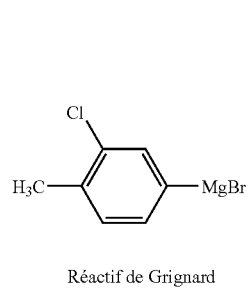

Réactif de Grignard

KEY: Mg (tournure) = Mg (chips); THF anhydre = anhydrous THF; Réactif de Grignard = Grignard's reagent 2$^{nd}$ Step: Coupling with di-t-butylazodicarboxylate Reaction scheme

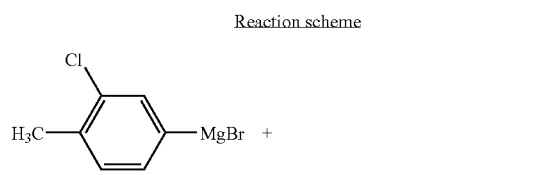

Réactif de Grignard

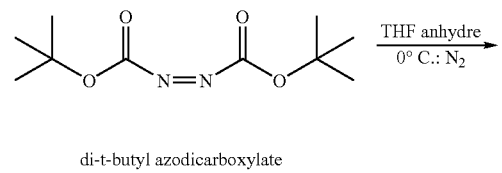

di-t-butyl azodicarboxylate

-continued

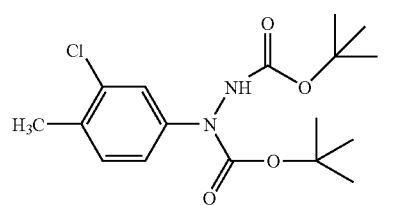

N,N'-bis-(t-butoxycarbonyll)-3-(chloro-p-tolyl)hydrazine

KEY: THF anhydre = anhydrous THF; Réactif de Grignard = Grignard's reagent

3$^{rd}$ step: Deprotection

Reaction Scheme

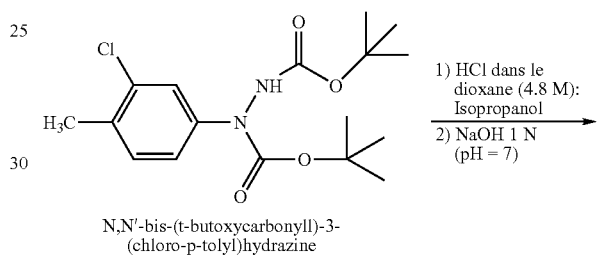

N,N'-bis-(t-butoxycarbonyll)-3-(chloro-p-tolyl)hydrazine

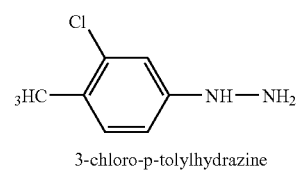

3-chloro-p-tolylhydrazine

KEY: HCl dans le dioxane (4.8 M) = HCl in dioxane (4.8 M)

4$^{th}$ Step: Coupling with Diphenylcarbonate

Reaction scheme

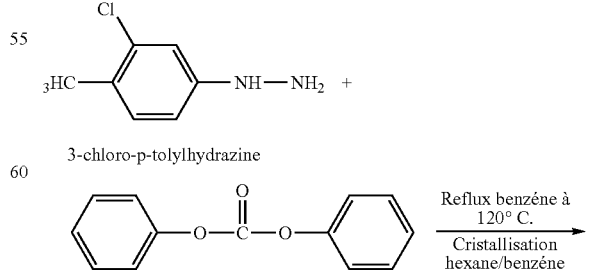

3-chloro-p-tolylhydrazine diphenylcarbonate

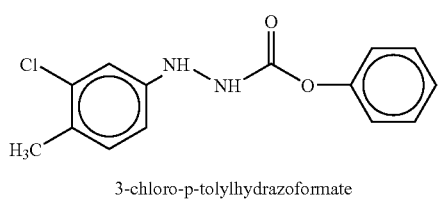

3-chloro-p-tolylhydrazoformate

KEY: reflux benzéne à 120° C. = benzene reflux at 120° C.; Cristallisation hexane/benzéne = hexane/benzene crystallization

5$^{th}$ Step: Coupling with Phenylalanine

Reaction Scheme

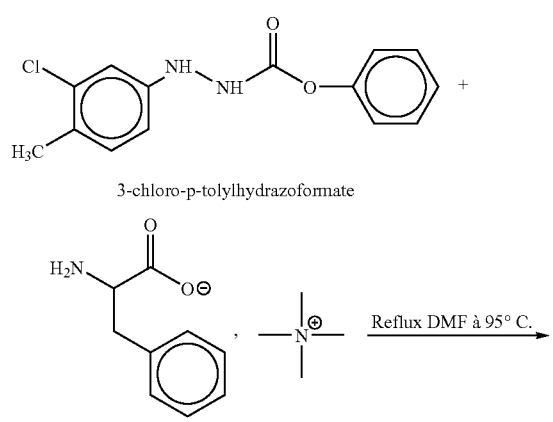

N-(3-chloro-p-tolylHydrazoFormyl)-L-PhenylAlanine

KEY: Sel de triethylammonium de la Phenylalanine = phenylalanine, triethylammonium salt; Reflux DMF à 95° C. = DMF reflux at 95° C.

6$^{th}$ Step: Oxidation; Change from "hydrazo" to "azo" Form

Reaction scheme

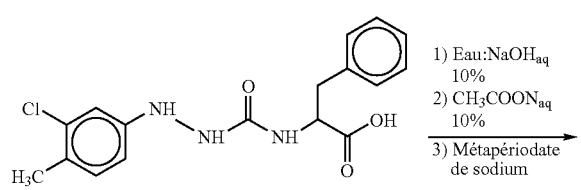

N-(3-chloro-p-tolylHydrazoFormyl)-L-PhenylAlanine

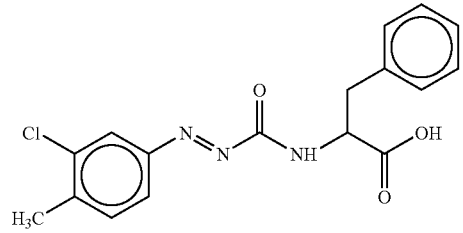

N-(3-chloro-p-tolylAzoFormyl)-L-PhenylAlanine

KEY: 1) Eau = 1) Water; 3) Métapériodate de sodium = 3) Sodium metaperiodate

7$^{th}$ Step: Coupling with Arginine

Reaction scheme

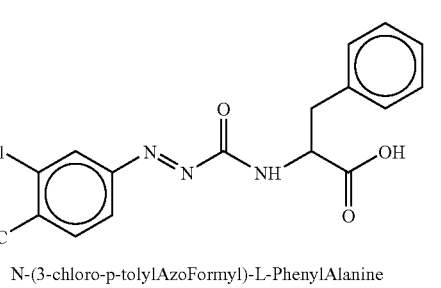

N-(3-chloro-p-tolylAzoFormyl)-L-PhenylAlanine

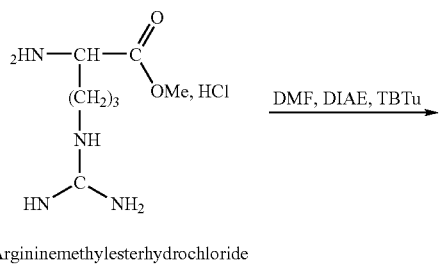

Argininemethylesterhydrochloride

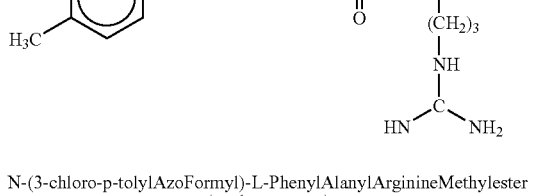

N-(3-chloro-p-tolylAzoFormyl)-L-PhenylAlanylArginineMethylester
(couleur orange)

KEY: (couleur orange) = (orange color)

8th Step: Saponification

Reaction scheme

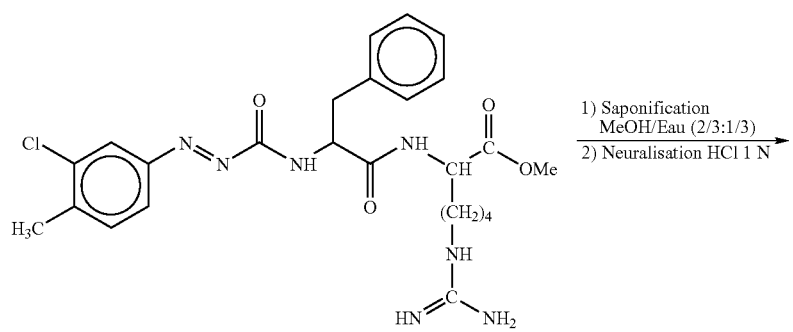

N-(3-chloro-p-tolylAzoFormyl)-L-PhenylAlanylArginineMethylester
(couleur orange)

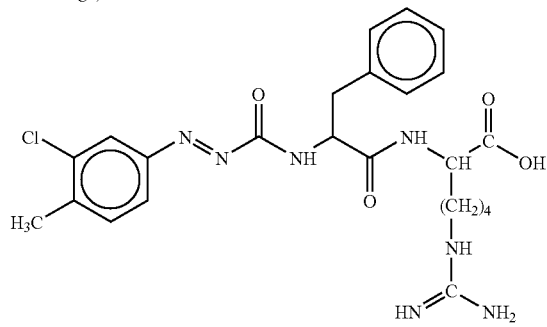

N-(3-chloro-p-tolylAzoFormyl)-L-PhenylAlanineArginine

KEY: MeOH/Eau = MeOH/Water; (couleur orange) = (orange color)

G/Synthesis of 3-chloro-p-tolylazoformylphenylalanylarginine (compound 7):

1st step: Grignard's Reagent

Reaction scheme

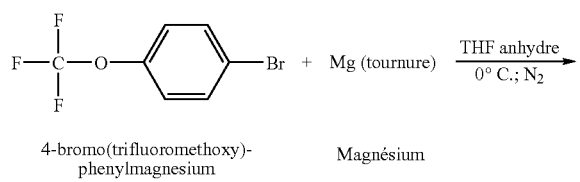

4-bromo(trifluoromethoxy)-
phenylmagnesium    Magnésium

-continued

KEY: Mg (tournure) = Mg (chips); THF anhydre = anhydrous THF; Réactif de Grignard = Grignard's reagent

2nd Step: Coupling with di-t-butylazodicarboxylate

Reaction scheme

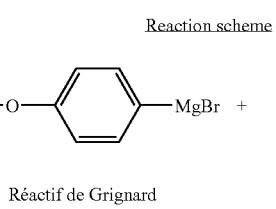

Réactif de Grignard

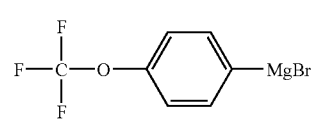

Réactif de Grignard

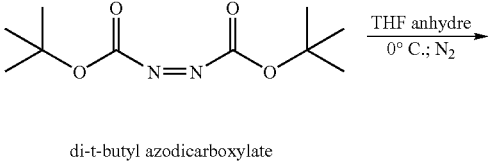

di-t-butyl azodicarboxylate

-continued

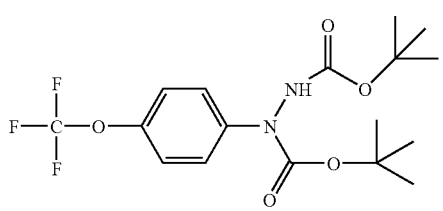

N,N'-bis-(t-butoxycarbonyll)-4-
(trifluoromethoxy)phenylhydrazine

KEY: THF anhydre = anhydrous THF; Réactif de Grignard = Grignard's reagent

3<sup>rd</sup> step: Deprotection

Reaction scheme

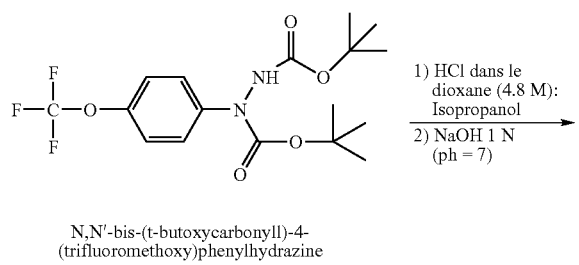

N,N'-bis-(t-butoxycarbonyll)-4-
(trifluoromethoxy)phenylhydrazine

1) HCl dans le dioxane (4.8 M): Isopropanol
2) NaOH 1 N (ph = 7)

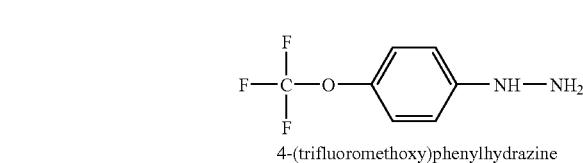

4-(trifluoromethoxy)phenylhydrazine

KEY: HCl dans le dioxane (4.8 M) = HCl in dioxane (4.8 M)

4<sup>th</sup> step: Coupling with Diphenylcarbonate

Reaction scheme

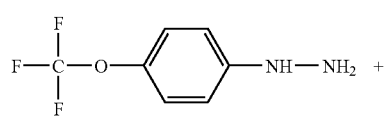

4-(trifluoromethoxy)phenylhydrazine

-continued

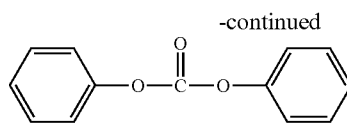

diphenylcarbonate

Reflux benzéne à 120° C.
Cristallisation hexane/benzéne

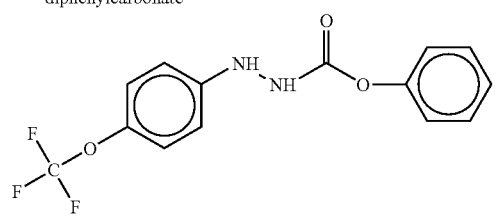

4-(trifluoromethoxy)phenylhydrazoformate

KEY: reflux benzene à 120° C. = benzene reflux at 120° C.; Cristallisation hexane/benzéne = hexane/benzene crystallization 5<sup>th</sup> Step: Coupling with Phenylalanine Reaction scheme

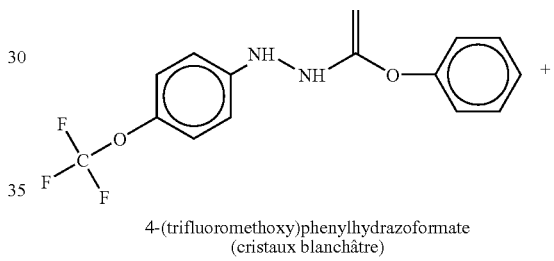

4-(trifluoromethoxy)phenylhydrazoformate
(cristaux blanchâtre)

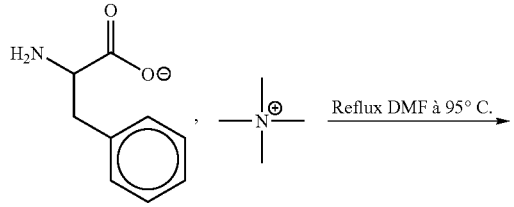

Sel de triethylammonium
de la Phenylalanine

Reflux DMF à 95° C.

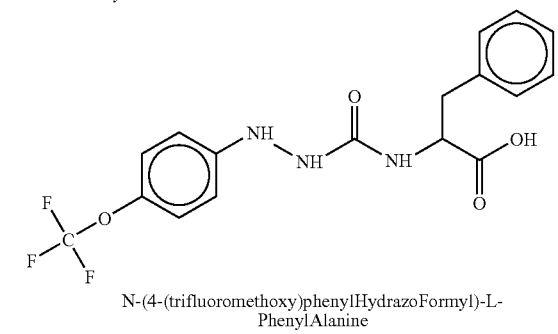

N-(4-(trifluoromethoxy)phenylHydrazoFormyl)-L-PhenylAlanine

KEY: Sel de triethylammonium de la Phenylalanine = phenylalanine, triethylammonium salt; Reflux DMF à 95° C. = DMF reflux at 95° C.

6th Step: Oxidation; Change from "hydrazo" to "azo" Form
7th Step: Coupling with Arginine
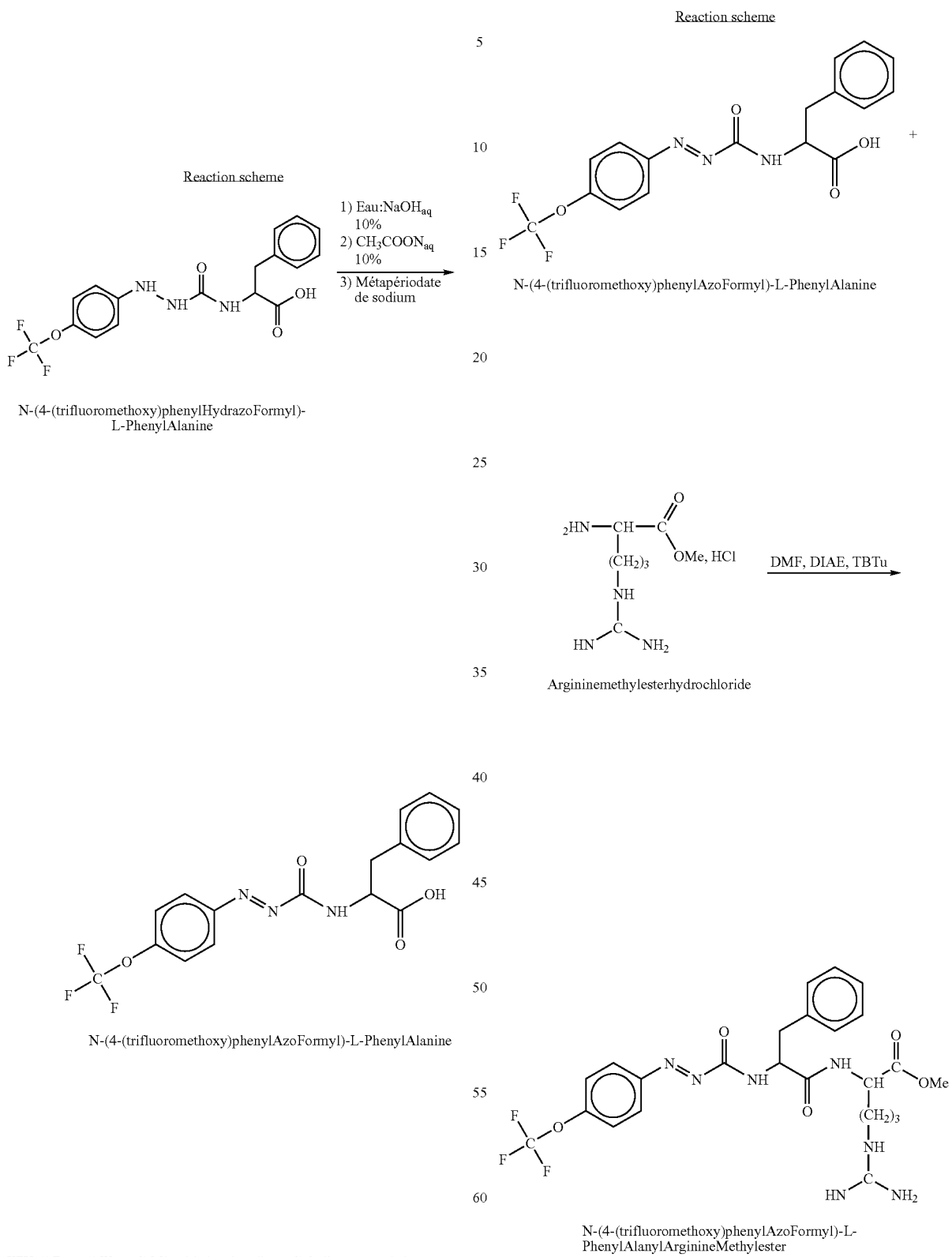
KEY: 1) Eau = 1) Water; 3) Métapériodate de sodium = 3) Sodium metaperiodate

8th Step: Saponification

Reaction scheme

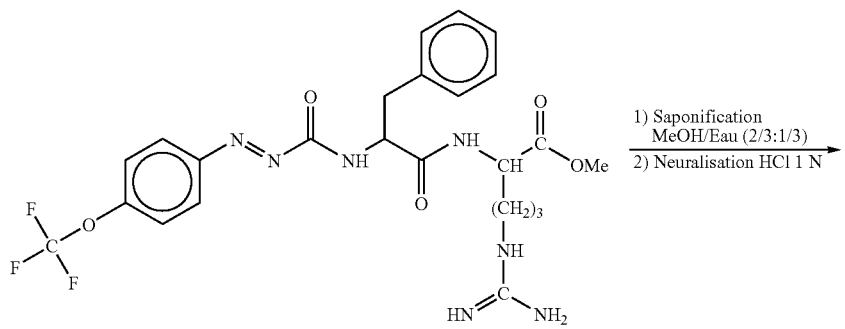

N-(4-trifluoromethoxy)phenylAzoFormyl)-L-PhenylAlanylArginineMethylester
(couleur orange)

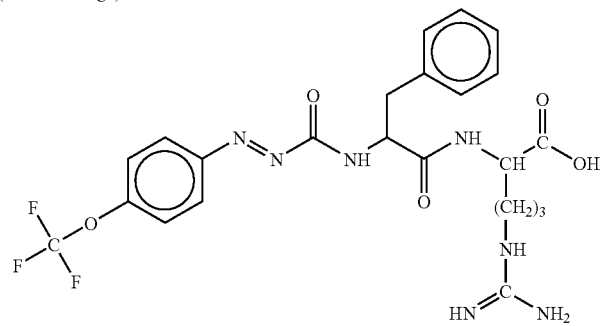

N-(4-trifluoromethoxy)phenylAzoFormyl)-L-PhenylAlanylArginine
(couleur orange)

KEY: MeOH/Eau = MeOH/Water; (couleur orange) = (orange color)

H/Synthesis of 4-methylthiophenylazoformylphenylalanylarginine (compound 8):

1st step: Grignard's Reagent

2nd Step: Coupling with di-t-butylazodicarboxylate

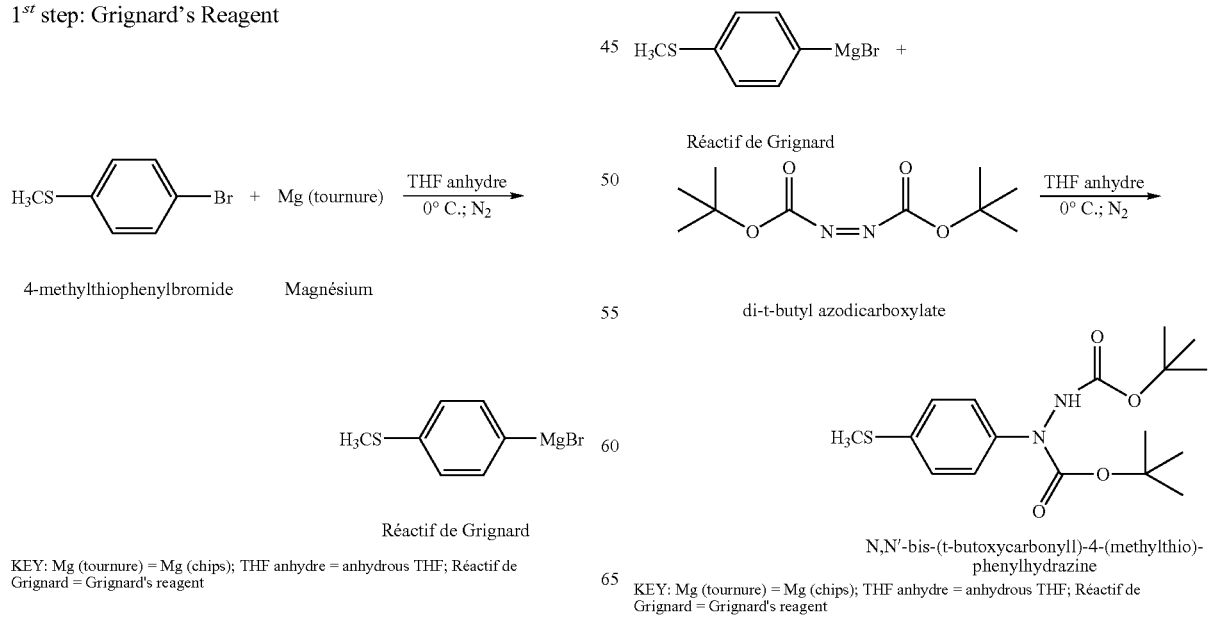

KEY: Mg (tournure) = Mg (chips); THF anhydre = anhydrous THF; Réactif de Grignard = Grignard's reagent

3rd Step: Deprotection

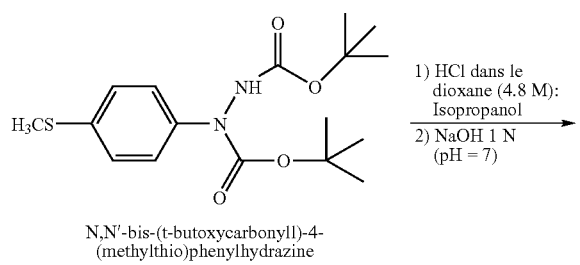

N,N'-bis-(t-butoxycarbonyl)-4-(methylthio)phenylhydrazine 4-(methylthio)phenylhydrazine KEY: HCl dans le dioxane (4.8 M) = HCl in dioxane (4.8 M)

4th Step: Coupling with Diphenylcarbonate

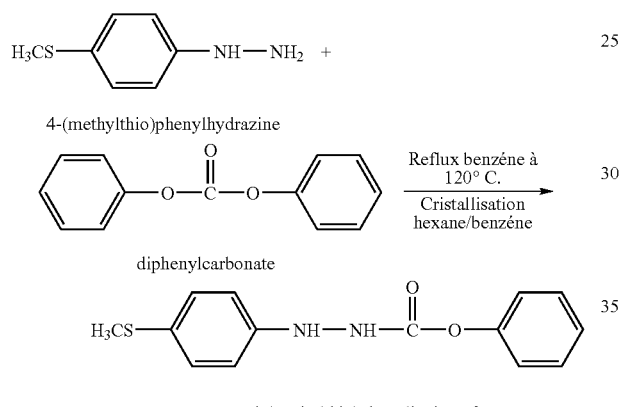

4-(methylthio)phenylhydrazine diphenylcarbonate 4-(methylthio)phenylhydrazoformate -continued KEY: reflux benzéne à 120° C. = benzene reflux at 120° C.; Cristallisation hexane/benzéne = hexane/benzene crystallization

5th Step: Coupling with Phenylalanine

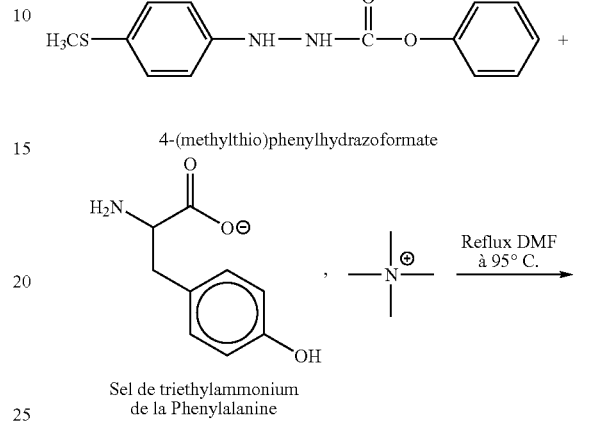

4-(methylthio)phenylhydrazoformate

Sel de triethylammonium de la Phenylalanine

N-(4-methylthioPhenylHydrazoFormyl)-L-Tyrosine

KEY: Sel de triethylammonium de la Phenylalanine = phenylalanine, triethylammonium salt; Reflux DMF à 95° C. = DMF reflux at 95° C.

6th Step: Oxidation; Change from "hydrazo" to "azo" Form

Reaction scheme

N-(4-methylthioPhenylHydrazoFormyl)-L-PhenylAlanine

1) Eau:NaOH$_{aq}$ 10%
2) CH$_3$COON$_{aq}$ 10%
3) Métapériodate de sodium

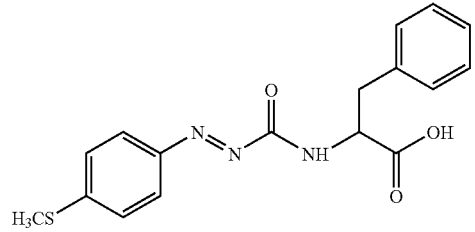
N-(4-methylthioPhenylHydrazoFormyl)-L-PhenylAlanine
KEY: 1) Eau = 1) Water; 3) Métapériodate de sodium = 3) Sodium metaperiodate
7<sup>th</sup> Step: Coupling with Arginine
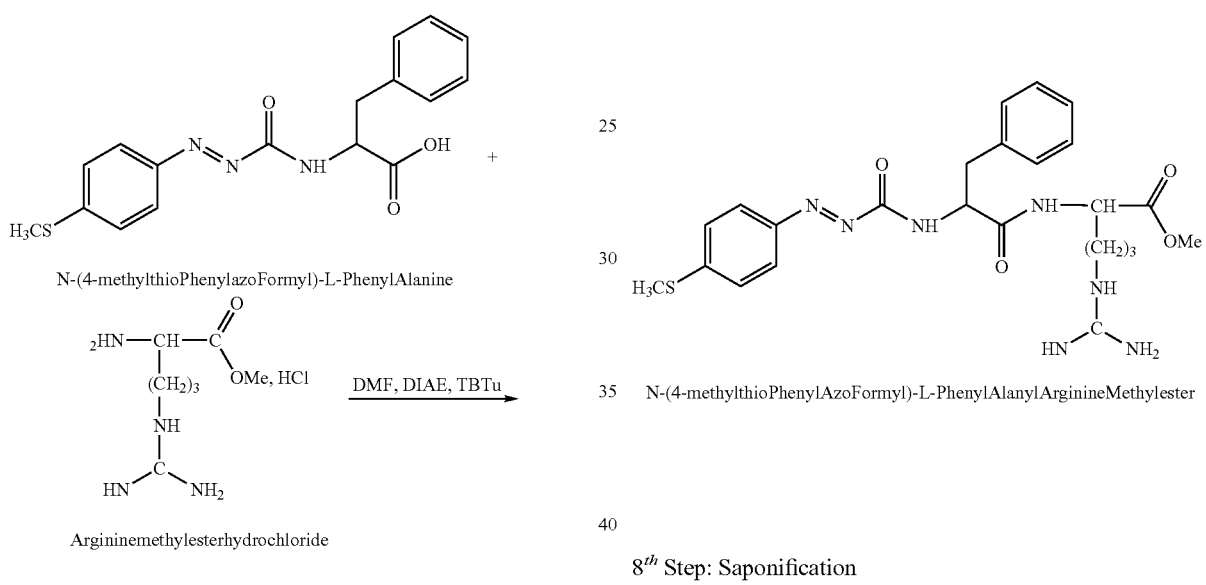
8<sup>th</sup> Step: Saponification
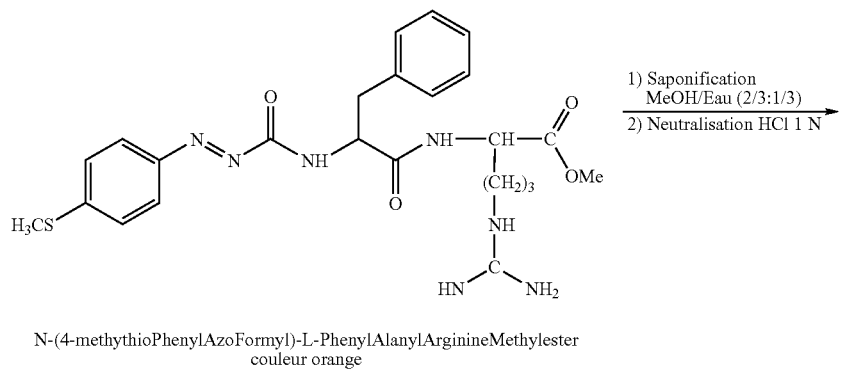
N-(4-methythioPhenylAzoFormyl)-L-PhenylAlanylArginineMethylester
couleur orange -continued

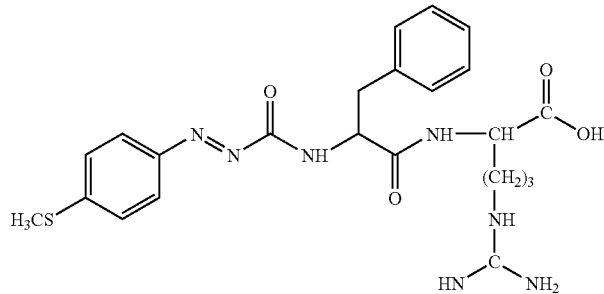

N-(4-methythioPhenylAzoFormyl)-L-PhenylAlanineArginine
Couleur orange

KEY: MeOH/Eau = MeOH/Water; (couleur orange) = (orange color)

I/Synthesis of 4-methylthiophenylazoformyltyrosylarginine (compound 9):

1st Step: Grignard's Reagent

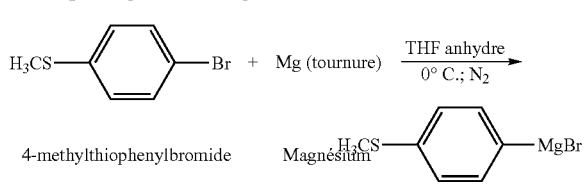

4-methylthiophenylbromide    Magnésium    Réactif de Grignard

KEY: Mg (tournure) = Mg (chips); THF anhydre = anhydrous THF; Réactif de Grignard = Grignard's reagent

2nd Step: Coupling with di-t-butylazodicarboxylate

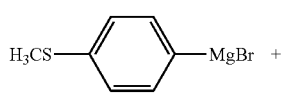

Réactif de Grignard di-t-butyl azodicarboxylate

N,N'-bis-(t-butoxycarbonyll)-4-(methylthio)-phenylhydrazine

KEY: THF anhydre = anhydrous THF; Réactif de Grignard = Grignard's reagent

3rd Step: Deprotection

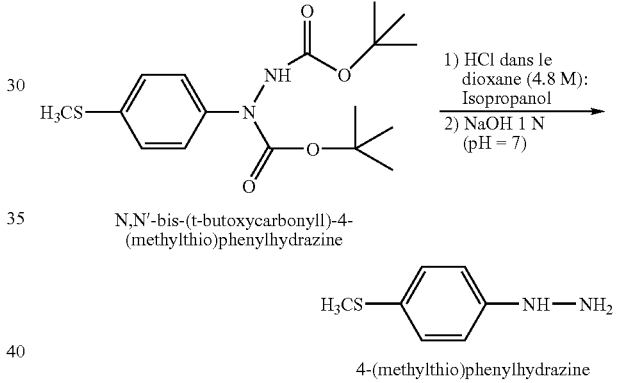

N,N'-bis-(t-butoxycarbonyll)-4-(methylthio)phenylhydrazine 4-(methylthio)phenylhydrazine KEY: HCl dans le dioxane (4.8 M) = HCl in dioxane (4.8 M)

4th Step: Coupling with Diphenylcarbonate

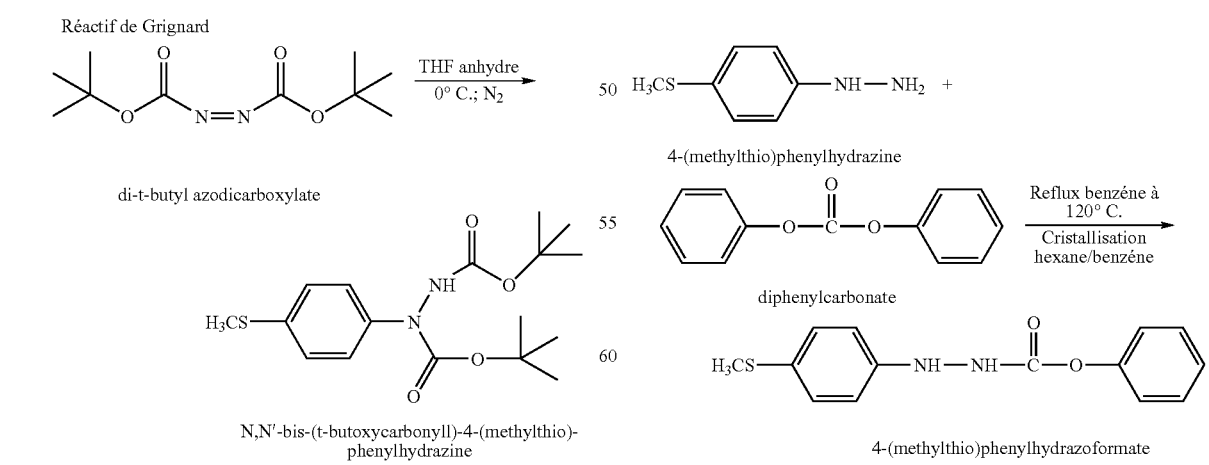

4-(methylthio)phenylhydrazine diphenylcarbonate 4-(methylthio)phenylhydrazoformate KEY: reflux benzéne à 120° C. = benzene reflux at 120° C.; Cristallisation hexane/benzéne = hexane/benzene crystallization

5th Step: Coupling with Tyrosine

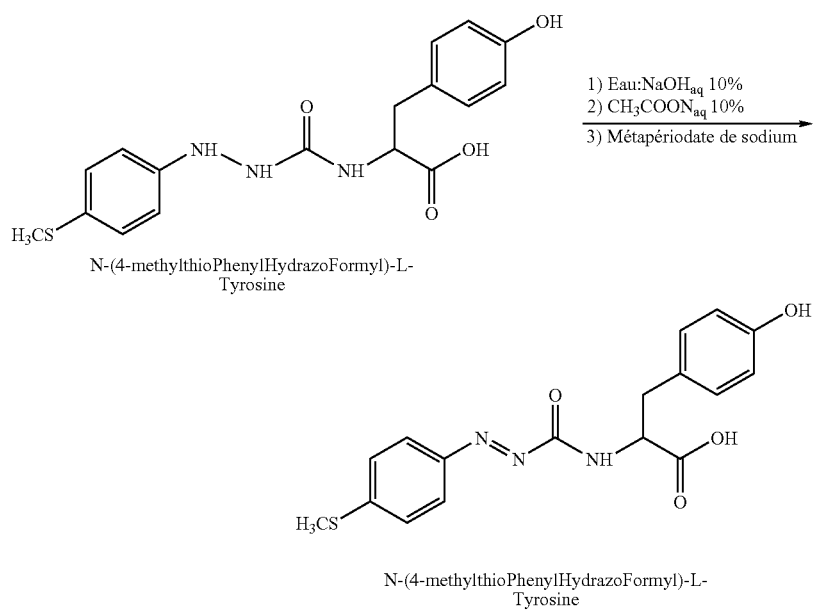

Sel de triethylammonium de la tyrosine

N-(4-methylthioPhenylHydrazoFormyl)-L-Tyrosine

KEY: Sel de triethylammonium de la tyrosine = tyrosine, triethylammonium salt; Reflux DMF à 95° C. = DMF reflux at 95° C.

6th Step: Oxidation; Change from "hydrazo" to "azo" Form

N-(4-methylthioPhenylHydrazoFormyl)-L-Tyrosine

1) Eau:NaOH$_{aq}$ 10%
2) CH$_3$COON$_{aq}$ 10%
3) Métapériodate de sodium

N-(4-methylthioPhenylHydrazoFormyl)-L-Tyrosine

KEY: 1) Eau = 1) Water; 3) Métapériodate de sodium = 3) Sodium metaperiodate

7th Step: Coupling with Arginine

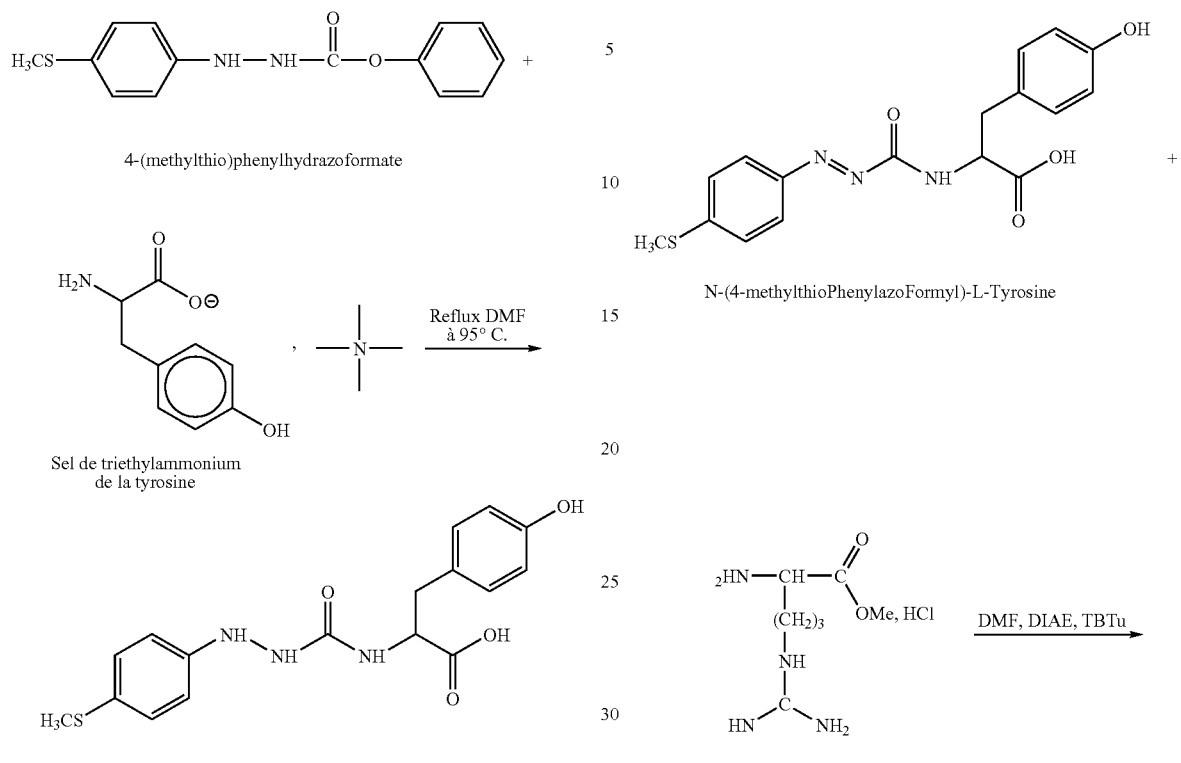

N-(4-methylthioPhenylazoFormyl)-L-Tyrosine

Argininemethylesterhydrochloride

DMF, DIAE, TBTu

-continued

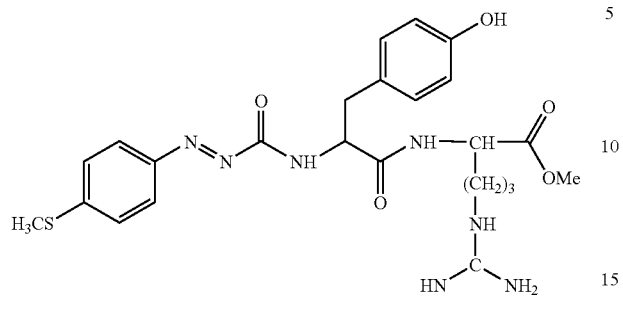

N-(4-methylthioPhenylAzoFormyl)-L-TyrosylArginineMethylester

EXAMPLE N° 2

1—Principle of Assay and Principal Reagents Employed

Principle of TAFIa Enzymatic Activity

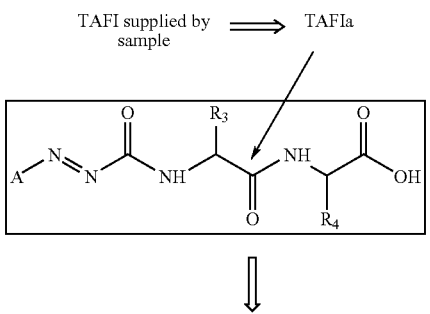

$8^{th}$ Step: Saponification

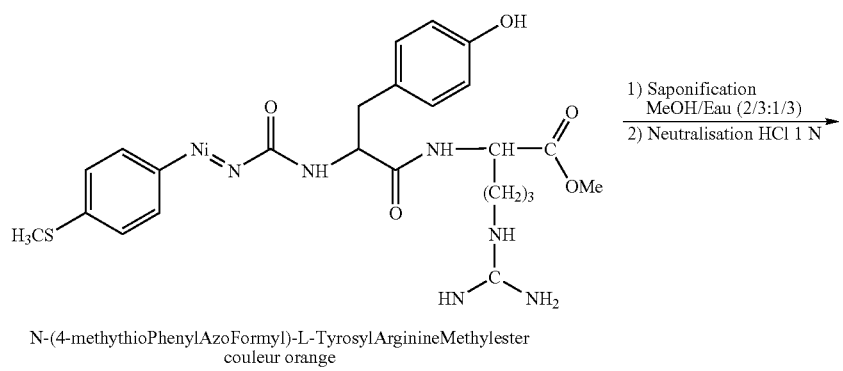

N-(4-methythioPhenylAzoFormyl)-L-TyrosylArginineMethylester
couleur orange

1) Saponification MeOH/Eau (2/3:1/3)
2) Neutralisation HCl 1 N

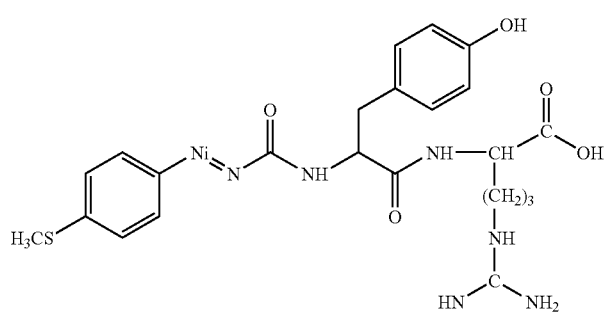

N-(4-methythioPhenylAzoFormyl)-L-TyrosylArginine
Couleur orange

KEY: MeOH/Eau = MeOH/Water; (couleur orange) = (orange color)

-continued

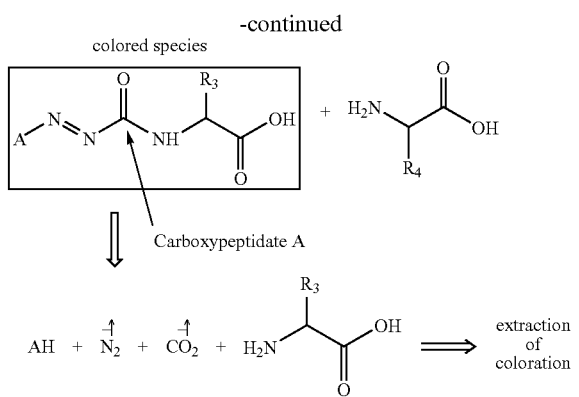

2. Example of Protocol for Assaying the Activity of TAFI in Accordance with the Method of the Invention a) $1^{st}$ Operating Mode: Thrombin-thrombomodulin Method.

The test plasma sample was divided into two aliquots, one being supplemented with PIC (Calbiochem—ref 217359), and the other with Hepes buffer.

The two aliquots were then treated in an identical way in accordance with the following principle:

Activation of TAFI
150 μl of plasma diluted 1/20 with Hepes buffer (or purified TAFI, 13 μg/ml in Hepes buffer);
10 μl of PIC or $H_2O$;
5 minutes at ambient temperature;
150 μl of coagulation activator buffer;
10 minutes at ambient temperature;
100 μl of PPACK+100 μl MxPAFFR (substrate) (5 mM).

TAFI Activity Test
30 minutes at ambient temperature;
100 μl HCl 1M+100 μl NaOH 1M;

Developing:
Dilution to 1/3 in Hepes buffer;
Read OD at 382 nm;
25 μl carboxypeptidase A;
Read OD at 382 nm for 1 minute.

Possible Variations of First Operating Mode:
the assay can be carried out at a temperature of 37° C.;
the substrate can be incorporated ab initio, at the same time as the activator buffer;
reading can be carried out by HPLC.

Preferred Final Concentrations for the Different Products:
PPACK: H-D-Phe-Pro-Arg-chloromethylketone, MW=451 30 μM (Bachem—ref n° 1065);
Pefabloc: it can be used in place of PPACK: 0.1 mM (Pentapharm—ref399.01);
Substrate (MxPAFFR): 1 mM;
Carboxypeptidase A: bovine pancreas origin (Sigma—ref C 0386).
Flask of 5.1 ml with 5000 units, 21 mg prot/ml, 47 units/mg of protein.
The CPA was filtered with a prefilter, a 5 μm filter and a 0.45 μm filter, to which ml of $H_2O$ was added.
PIC: used at 7 μM
1 mg of PCI can inhibit about 8 mg of TAFI (50 U/mg) at 50% as indicated by the manufacturer (Calbiochem).
The concentration of 30 μM of PPACK would correspond to an initial concentration of 150 μM. The final concentration of 1 mM of substrate would correspond to an initial concentration of 5 mM. The final concentration of 7 μM of CPI would correspond to an initial concentration of 0.38 mM.

The inventors observed that the concentrations indicated above can be modified to use a final concentration of PPACK reduced to 4 μM and a reduced final concentration of substrate.

Activator Buffer:
The preferred route to activating coagulation in the present invention is activation route by the thrombin/thrombomodulir complex. In this case, the activator buffer employed comprises the following constituents:
37 μl of thrombomodulin from 0 to 80 nM and preferably 10 nM (rabbit lung thrombomodulin—American Diagnostica—ref 237);
6 μl of thrombin from 0.2 to 10 NIH/ml and preferably 0.8 NIH/ml (Diagnostica Stago—research product);
750 μl of calcium chloride from 0 to 80 nm, preferably 40 nM;
705 μl of Hepes buffer, 9.4 mM, pH=7.6.

The concentrations are given for a final volume of 1498 μl of activator buffer.

NB: Hepes buffer contains: 20 mM Hepes, 4 mM KCl and 1% BSA. Other tests were carried out with 20 mM Hepes and 150 mM NaCl.

As indicated in the description, other activation routes are possible, especially the activation route by factor XIa.
In this case, an example of activator buffer contains the following constituents:
5 μl of thrombomodulin, 30 U/ml;
30 μl of pure factor XIa (Calbiochem—ref 233483);
88 μl Hepes buffer, pH=7.4 (Hepes 20 mM and NaCl 150 mM).

The concentrations are given by way of example and can be readjusted by the skilled person.

b) $2^{nd}$ Operating Mode: Thrombin Generation Method.

A further activation route of coagulation involves thrombin and requires the implementation of an activator for the contact phase.

| | Thrombin generation |
|---|---|
| 1) TAFI activation | 100 μl of sample ± 10 μl CPI |
| | 100 μl activator buffer composed of: |
| | 30 μl of thrombomodulin, 30 U/ml; |
| | 165 μl of contact phase activator; |
| | 800 μl of 20 mM $CaCl_2$; |
| | Incubation 10 min, TA |
| | 100 μl of PPACK |
| 2) TAFIa activity test | 100 μl substrate |
| | incubation 30 min TA |
| | 100 μl 1 N HCl |
| | 100 μl 1 N NaOH |
| 3) developing | dilution of |
| | 250 μl of reaction medium by |
| | 500 μl of buffer + 50 μl of $H_2SO_4$ |
| | read $OD_1$ |
| | or |
| | 250 μl buffer + 250 μl CPa |
| | incubate 5 min TA |
| | 50 μl $H_2SO_4$ |
| | read $OD_2$ 405 nm |

EXAMPLE N° 3

Establishing a Calibration Curve in the Thrombin/thrombomodulin Method

Figure 3:
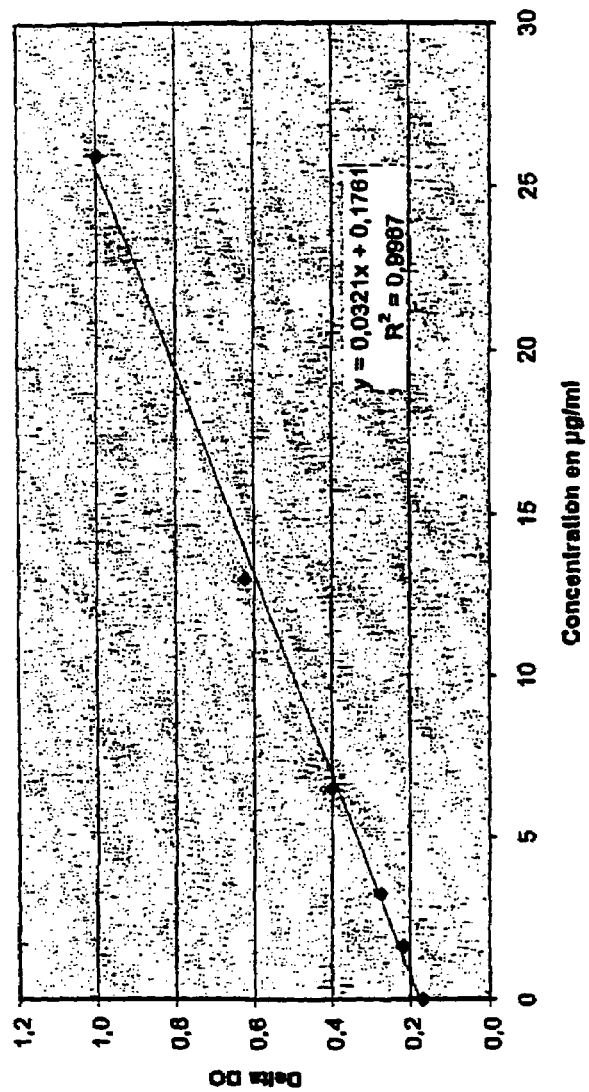
FIG. 3: Calibration curve established from a TAFI deficient plasma, overloaded with purified TAFI to obtain a concentration range of 0 to 26 µg/ml.

FIG. 3 below shows a calibration curve established from a plasma deficient in TAFI overloaded with purified TAFI to obtain a range of TAFI concentrations of 0 to 26 µg/ml.

The compound with formula I used was MxPAAFR in a concentration of 5 mM.

The ΔODs measured in accordance with the method of the invention are shown in Table III below:

TABLE III

| | Concentration of TAFIa (µg/ml) | | | | | |
|---|---|---|---|---|---|---|
| | 0 | 1.63 | 3.25 | 6.5 | 13 | 26 |
| ΔOD measured | 0.168 | 0.217 | 0.273 | 0.399 | 0.624 | 0.995 |

As can be seen in FIG. 3, the calibration curve is linear for the concentration range being studied. This broadly covers the zone of normality, TAFI being present in the organism in concentrations of 5 to 15 µg/ml.

Thus, the method of the invention allows both deficits and abnormally high levels of TAFI to be detected.

EXAMPLE N° 4

Results Obtained for Different Plasma Types

The method of the invention was applied to different plasma types using the protocol described in Example N° 2.

Fresh Plasma, Frozen Plasma:

The assay can be carried out on fresh or frozen plasma, but a reduction in OD is observed between the two. This results from a slight degradation of TAFI during defrosting (the protein degrades).

| Fresh plasma | Frozen plasma |
|---|---|
| 9.4 µg/ml | 6.0 µg/ml |
| 11.2 µg/ml | 6.5 µg/ml |
| 10.7 µg/ml | 5.6 µg/ml |

Frozen Plasma, Freeze-dried Plasma:

TAFI assay is possible for freeze-dried plasma and is similar to frozen plasma.

| | Frozen plasma | Freeze-dried plasma |
|---|---|---|
| ΔOD | 0.302 | 0.354 |

Frozen Plasma of Different Origins:

| Thrombolytic | 2.9 µg/ml |
|---|---|
| CIVD | 2.8 µg/ml |
| Cirrhosis | 1.4 µg/ml |
| Maternity | 7.1 µg/ml |
| Hyperfibrinogenemia | 4.6 µg/ml |
| HNF | 6.1 µg/ml |
| | (heparins not fractionated) |
| AVK | 5.8-8.2-6.5-7.1 µg/ml (anti-vitamin K) |

EXAMPLE N° 5

Assay Carried Out with Different Substrates of the Invention

The method of the invention was applied to a solution containing purified TAFI with different compounds described in Example N° 1.

The test was carried out on a solution of 6.5 µg/ml of purified TAFI in Hepes buffer. The results are shown in Table IV below.

TABLE IV

| Compounds | Reading | Starting OD | Final OD | Delta OD |
|---|---|---|---|---|
| 2,3 DMPAFFR 5 mM | 350 nm | 0.318 | 0.089 | 0.229 |
| 2,4 DMPAFFR 5 mM | 330 nm | 1.004 | 0.087 | 0.917 |
| 2,5 DMPAFFR 5 mM | 320 nm | 0.973 | 0.131 | 0.842 |
| AAFFK 5 mM | 320 nm | 0.973 | 0.131 | 0.842 |

EXAMPLE N° 6

Specificity of TAFIa for Compounds with Formula (I) in Accordance with the Invention:

The example below aims to demonstrate the necessity of using the method and compounds with formula (I) of the invention to specifically assay the activity of CPNs or Us, in particular TAFI, compared with other basic carboxypeptidases.

1/ In this case, the assay was carried out with a substrate from the family of compounds described by Mock in (14). This substrate was constituted by a single amino acid carrying an anizylazoformyl chromophoric radical ($CH_3OC_6H_4$—N=N—CO— portion). The amino acid selected was arginine, a basic amino acid normally hydrolyzed by carboxypeptidases B (1).

This substrate is hereinafter termed AAFR (anizylazoformylarginine) or MxAFR (4-methoxyphenylazoformylarginine).

This substrate (0.25 mM) was brought into the presence of either a sample of plasma TAFI or a solution of porcine pancreatic carboxypeptidase B (Sigma, Reference: C9584), 5.2 mol/l.

The reduction in coloration of each of the two samples was followed using a spectrophotometer. Each sample was treated using the protocol below:

a) Starting sample:
   plasma TAFI (present in a normal plasma pool—diluted to 1/20); or
   porcine pancreatic carboxypeptidase B, 5.2 mol/l (in Hepes buffer);
b) activation with thrombin-thrombomodulin-$CaCl_2$ complex (see Example N° 2) for the plasma TAFI sample;
c) addition of 5 mM AAFR;
d) read OD at 382 nm.

Results:

| at 382 nm | Starting OD | Final OD | Delta OD |
|---|---|---|---|
| Porcine CPB | 1.054 | 0.445 | 0.608 |
| Plasma TAFIa | 1.730 | 1.681 | 0.049 |

Conclusion:

Activated TAFI does not hydrolyze AAFR, in contrast to pancreatic CPB.

2/ The method of the invention was then applied to a solution of purified TAFI either with a substrate with formula (I) (MxPAFFK) or with MxAFR to verify that TAFIa nevertheless hydrolyzes a compound with formula (I). Coagulation activation was triggered by the thrombin-thrombomodulin-$CaCl_2$ complex (see protocol in Example N° 2).

The reduction in coloration of each of the two samples was followed using a spectrophotometer.
a) Starting samples: purified TAFI solution, 18 μg/ml (diluted in Hepes buffer);
b) activating coagulation;
c) adding 27 mM MxAFR or MXPAFFK (control), concentration of MxAFFK;
d) adding CPA to the sample containing the MxPAFFK;
e) read OD at 382 nm.

Results:

| | Starting OD | Final OD | Delta OD |
|---|---|---|---|
| TAFIa + MxAFR | 1.356 | 1.300 | 0.056 |
| TAFIa + MxPAFFK | 1.397 | 0.849 | 0.548 |

Conclusion:

Activated TAFI does not hydrolyze MXAFR, although it is active on MxPAFFK.

EXAMPLE N° 7

Thrombin Generation Methodology

A range was produced as described in Example N° 2, operating mode b), by diluting a plasma pool (FIG. 4).

| Plasma | Delta OD | Concentration, μg/ml |
|---|---|---|
| N control system | 0.848 | 7.69 |
| P control system | 0.670 | 4.90 |
| Normal plasma | 0.928 | 9.39 |

This methodology allowed plasmas to be distinguished as a function of their capacity to generate thrombin. It was a better reflection of the hypercoagulatability condition of the patient.

BIBLIOGRAPHY

1. BOUMA. B. N. et al : "Thrombin-Activatable Fibrinolysis Inhibitor (TAFI, Plasma Procarboxypeptidase B, Procarboxypeptidase R, Procarboxypeptidase U)". Thromb. Research, 101 :329-354,2001.
2. BAJZAR L. : "Purification and Characterization of TAFI, a Thrombin-activable Fibrinolysis Inhibitor". J. of Biol. Chem., 270, 24:14477-14484, 1995.
3. JUHAN-VAGUE I., ALESSI M.-C. : "TAFI: lien moléculaire entre les processus de coagulation et de fibrinolyse". Sang Thrombose Veineuse, 5, 10:314-6, 1998.
4. SCHATTEMAN K. et al.: "Carboxypeptidase U at the interface between coagulation and fibrinolysis". Clin. Appl. Thrombosis/Hemostasis, 7 {2}:93-101, 2001.
5. WOLF M. et al. : "The kinetics of carboxypeptidase B activity". J. of Biol. Chem., 237, n° 10, October 1962.
6. SUZUKI S. et al.: "Spectrophotometric determination of glycine with 2,4,6-Trichloro-s-Triazine". Analytical Chemistry, Vol. 42, N° 1, January 1970.
7. LORENTZ K. et al.: "Determination of carboxypeptidase B in duodenal contents". Clinica Chimica Acta, 37:515-517,1972.
8. PLUMMER Th. H. et al.: "An improved spectrophotometric assay for human plasma carboxypeptidase N". Analytical Biochemistry, 108:348-353, 1980.
9. FISCHER G. H. et al. : "Synthetic inhibitors of carboxypeptidase N". Adv. Experimental Med. Biol., 198, Part A, 405-410, 1986.
10. SARUTA H. et al. : "Colorimetric determination of carboxypeptidase A activity in serum". Clin. Chem. 32:5, 748-751, 1986.
11. NAM-JOO HONG et al.: "Development of substrate for carboxypeptidase B by employing Thiaarginine peptides". Bull Korean Chem. Soc., Vol. 19, N° 2, 189-93, 1998.
12. MOCK W. L. et al. : "Arazoformyl Dipeptide Substrates for Thermolysin. Confirmation of a Reverse Protonation Catalytic Mechanism". Biochemistry, 35: 7369-7377, 1996.
13. MOCK W L et al: "Arazoformyl Peptide Surrogates as Spectrophotometric Kinetic Assay Substrates for Carboxypeptidase A". Analytical Biochemistry, 239:218-222, 1996.
14. MOCK W. L. et al.: "Catalytic activity of carboxypeptidase B and of carboxypeptidase Y with anisylazoformyl substrates". Bioorganic & Medicinal Chemistry Letters, 9:187-192, 1999.
15. HATTON M. W.: "Studies on the coagulant enzyme from *Agkistrodon rhodostoma* venom. Isolation and some properties of the enzyme". Biochem. J., 131(4):799-807, 1973.
16. STOCKER K. et al.: "The coagulant enzyme from *Bothrops atrox* venom (batroxobin)". Methods Enzymol. 45:214-223, 1976.
17. DENSON K. W .E. : "Clot-inducing substances present in such venoms with particular reference to *Echis carinatus* venom". Thromb. Res., 8:351-360, 1976.
18. ROSING J. et al. : "Structural and functional properties of snake venom prothrombin activators". Toxicon, 30(12): 1515-1527,1992.

What is claimed is:

1. A compound of the following formula:

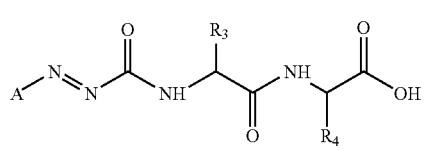

wherein:

A = [structures: substituted phenyl with R₁, R₂; substituted pyridine with R₁, R₂; substituted pyrimidine with R₁, R₂; substituted quinoline with R₁, R₂]

$R_1$ and $R_2$ may be the same or different and are H, —CH$_3$, —CH(CH$_3$)$_2$, —OCH$_3$, —Cl, —CF$_3$, —OCF$_3$, or —SCH$_3$;

$R_3$ is an amino acid radical hydrolysable by a carboxypeptidase A; and $R_4$ is a basic amino acid radical.

2. A compound according to claim 1, wherein:

$R_3$ is a hydrophobic amino acid radical; and $R_4$ is an arginine or lysine radical.

3. A compound according to claim 1 wherein $R_1$ is H and $R_2$ is —S—CH$_3$.

4. A compound according to claim 1 wherein $R_3$ is selected from the group consisting of:

tyrosine;
phenylalanine;
alanine;
valine;
leucine;
isoleucine; and
phenylglycine.

5. A compound according to claim 1 wherein $R_3$ is phenylalanine.

6. A compound according to claim 1 wherein $R_3$ is phenylalanine or tyrosine and $R_4$ is arginine or lysine.

7. A compound according to claim 1 wherein $R_3$ is tyrosine.

8. A compound according to claim 1, wherein $R_1$ is selected from the group consisting of: —H and —CH$_3$, and $R_2$ is selected from the group consisting of CH$_3$, O—CH$_3$ and —S—CH$_3$.

9. A compound according to claim 1, wherein A is:

[structure: phenyl with R₁, R₂]

10. A compound according to claim 1 wherein:

A = [structure: phenyl with R₁, R₂]

and wherein $R_1$, $R_2$, $R_3$ and $R_4$ are:

$R_1$ = —CH$_3$ $R_2$ = —CH$_3$ $R_3$ = —CH$_2$-phenyl
(2)* (3)*

$R_4$ = —(CH$_2$)$_3$—NH—C(=NH)—NH$_2$ $R_1$ = —CH$_3$
(2)*

$R_2$ = —CH$_3$ $R_3$ = —CH$_2$-phenyl
(4)*

$R_4$ = —(CH$_2$)$_3$—NH—C(=NH)—NH$_2$ $R_1$ = —CH$_3$
(2)*

$R_2$ = —CH$_3$ $R_3$ = —CH$_2$-phenyl
(5)*

$R_4$ = —(CH$_2$)$_3$—NH—C(=NH)—NH$_2$ $R_1$ = —H $R_2$ = —O—CH$_3$ $R_3$ = —CH$_2$-phenyl $R_4$ = —(CH$_2$)$_3$—NH—C(=NH)—NH$_2$ $R_1$ = —H $R_2$ = —O—CH$_3$ $R_3$ = —CH$_2$-phenyl $R_4$ = —(CH$_2$)$_4$—NH$_2$ $R_1$ = —Cl $R_2$ = —CH$_3$ $R_3$ = —CH$_2$-phenyl $R_4$ = —(CH$_2$)$_3$—NH—C(=NH)—NH$_2$ $R_1$ = —H $R_2$ = —O—CF$_3$ $R_3$ = —CH$_2$-phenyl $R_4$ = —(CH$_2$)$_3$—NH—C(=NH)—NH$_2$ $R_1$ = —H $R_2$ = —SCH$_3$ $R_3$ = —CH$_2$-phenyl $R_4$ = —(CH$_2$)$_3$—NH—C(=NH)—NH$_2$ $R_1$ = —H $R_2$ = —SCH$_3$ $R_3$ = —CH$_2$-phenyl-OH $R_4$ = —(CH$_2$)$_3$—NH—C(=NH)—NH$_2$ wherein the numbers designated with an asterix determine the position of the methyl groups on the phenyl radical.

11. A compound according to claim 1, wherein said compound is 4-methylthiophenylazoformyltyrosine arginine.

12. A method for assaying the activity of a carboxypeptidase N or a carboxypeptidase U in a biological sample, in which:

said sample is brought into contact with a compound of the formula (I) according to claim 1, and with a carboxypeptidase A, under conditions that allow hydrolysis of the sample; and the reduction in coloration of the sample containing the substrate of the formula (I) and carboxypeptidase A is measured, resulting from double hydrolysis of the substrate of the formula (I) by the CPN or CPU of the sample and by CPA.

13. A method according to claim 12, wherein $R_1$ is H and $R_2$ is —S—CH$_3$.

14. A method according to claim 12, wherein $R_4$ is an arginine or lysine radical.

15. A method according to claim 12, wherein the substrate is a compound of the formula (I) in which $R_3$ is selected from the following amino acid radicals:
- tyrosine;
- phenylalanine;
- alanine;
- valine;
- leucine;
- isoleucine; and
- phenylglycine.

16. A method according to claim 12, wherein $R_3$ is tyrosine.

17. A method according to claim 12, wherein the substrate is a compound of the formula (I), in which $R_3$ represents phenylalanine.

18. A method according to claim 12, wherein the substrate is a compound of the formula (I) in which $R_3$ represents phenylalanine and $R_4$ represents arginine or lysine.

19. A method according to claim 12, wherein the substrate is a compound of the formula (I) in which $R_1$ is selected from —H and —CH$_3$, and $R_2$ is selected from CH$_3$, O—CH$_3$ and —S—CH$_3$.

20. A method according to claim 12, wherein the substrate is a compound of the formula (I) in which:

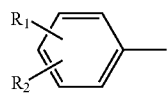

-A = in which:
  $R_1$ and $R_2$=H, —CH$_3$, —CH(CH$_3$)$_2$, —OCH$_3$, —Cl, —CF$_3$, —OCF$_3$, or —SCH$_3$;
  $R_3$=an amino acid radical hydrolysable by a carboxypeptidase A;
  $R_4$=a basic amino acid radical.

21. A method according to claim 12, wherein the substrate is a compound of the formula (I) in which:

-A =

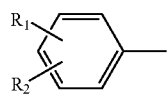

said compound being selected from the group constituted by the following compounds:

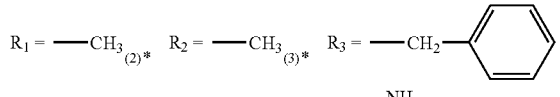
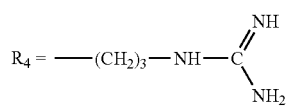
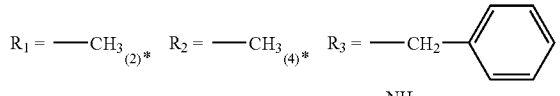
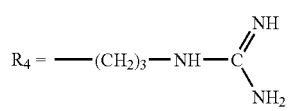
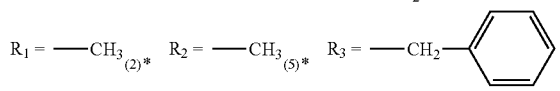
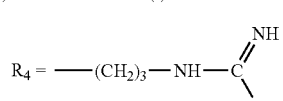
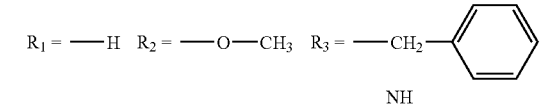
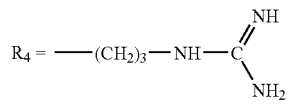
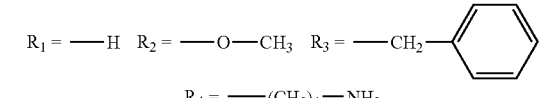
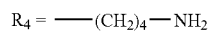
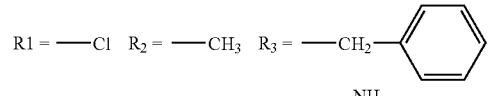
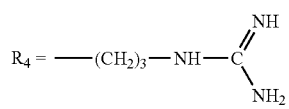
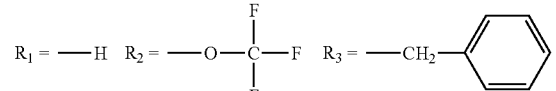
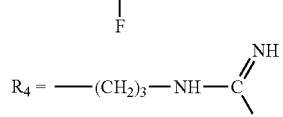
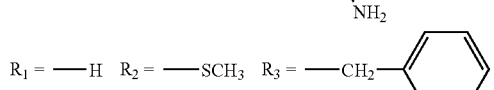
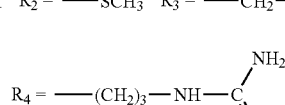
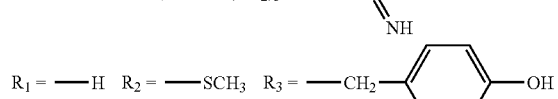
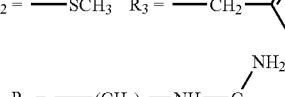
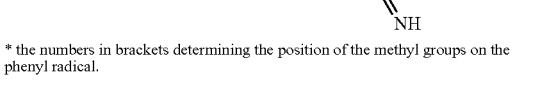
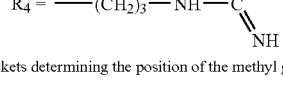

* the numbers in brackets determining the position of the methyl groups on the phenyl radical.

22. A method according to claim 12, in which the compound of the formula (I) is 4-MTPAFYR (4-methylthiophenylazoformyltyrosine arginine).

23. A method according to claim 12, wherein the optical density of the mixture is measured without adding CPA, then after adding CPA.

24. A method according to claim 12, wherein the measured decrease in coloration is compared with values on a calibration curve.

25. A method according to claim 12, wherein the sample is a blood sample.

26. A method according to claim 25, wherein the sample is plasma.

27. A method according to claim 12, wherein the CPA is pancreatic CPA.

28. A method according to claim 12, wherein the test sample is brought into the presence of an activator buffer for the time necessary to obtain activation of the carboxypeptidase U the activity of which is to be measured, then into the presence of a protease serine inhibitor.

29. A method according to claim 28, wherein the substrate of the formula (I) is added at the same time as the activator buffer, or simultaneously or immediately after the serine protease inhibitor.

30. A method according to claim 28, wherein activation is carried out using the thrombin/thrombomodulin complex route.

31. A method for assaying the activity of the constitutional CPN or CPU of a sample and that of the activatable CPN or CPU of the same sample, wherein the hydrolysis activity of the sample on a sample of the formula (I) is compared after bringing the sample into the presence of an activator buffer, if necessary for the time necessary to obtain activation of the carboxypeptidase U the activity of which is to be measured, then into the presence of a protease seine inhibitor, the observed hydrolysis activity being compared with the hydrolysis activity of the sample on a substrate of the formula (I) in the absence of an activator buffer in accordance with claim 12.

32. A method according to claim 21, wherein the carboxypeptidase is a CPU.

33. A method according to claim 32, wherein the CPU is TAFI.

34. A method according to claim 28, wherein the sample is treated in the presence and in the absence of a specific TAFI inhibitor wherein said TAFI inhibitor is added before sample activation.

35. A method according to claim 34, wherein the specific TAFI inhibitor is CPI.

36. A method for assaying activated TAFI in a blood sample, comprising the following steps:
 a) bringing a first aliquot of the sample into contact with a specific TAFI inhibitor and treating it using the method defined in claim 28;
 b) treating a second aliquot of the sample using the method of claim 28, in the absence of specific TAFI inhibitor;
 c) measuring the $\Delta$ OD between the first and second aliquot, representative of the activity of the activated TAFI in the sample.

37. A method according to claim 36 for differentiating between the activity of constitutional TAFI and that of activatable TAFI in the same sample, characterized in that the hydrolysis activity of a third aliquot of the sample is measured on a substrate of the formula (I) in the absence of a buffer activator.

38. A kit for assaying the activity of a CPN or a CPU in a sample comprising a chromogenic substrate constituted by a compound according to claim 1.

39. A kit for assaying the activity of TAFI in a biological sample, comprising:
 a TAFI activator buffer;
 carboxypeptidase A;
 a substrate of the formula (I) according to claim 1; and
 a TAFI inhibitor.

\* \* \* \* \*

UNITED STATES PATENT AND TRADEMARK OFFICE
CERTIFICATE OF CORRECTION

PATENT NO. : 7,405,280 B2 Page 1 of 1
APPLICATION NO. : 10/751601
DATED : July 29, 2008
INVENTOR(S) : Gérard Quentin It is certified that error appears in the above-identified patent and that said Letters Patent is hereby corrected as shown below:

Column 2, line 40, "a" should read "α".

Column 73, line 16, delete "or".

Column 77, line 38, "(D)" should read "(I)".

Signed and Sealed this

Twenty-seventh Day of October, 2009

David J. Kappos
*Director of the United States Patent and Trademark Office*